(12) United States Patent
Wyrwa et al.

(10) Patent No.: US 7,534,780 B2
(45) Date of Patent: May 19, 2009

(54) ESTRADIOL PRODRUGS

(75) Inventors: Ralf Wyrwa, Oelknitz (DE); Sven Ring, Jena (DE); Peter Droescher, Weimar (DE); Alexander Hillisch, Velbert (DE); Walter Elger, Berlin (DE); Birgitt Schneider, Jena (DE); Gudrun Reddersen, Jena (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 541 days.

(21) Appl. No.: 11/133,431

(22) Filed: May 20, 2005

(65) Prior Publication Data

US 2005/0288267 A1    Dec. 29, 2005

Related U.S. Application Data

(60) Provisional application No. 60/572,964, filed on May 21, 2004.

(30) Foreign Application Priority Data

May 21, 2004    (DE)  ........................ 10 2004 025 966

(51) Int. Cl.
*A61K 31/56* (2006.01)
*C07J 1/00* (2006.01)

(52) U.S. Cl. ...................................... 514/182; 552/626

(58) Field of Classification Search ................. 552/626; 514/182
See application file for complete search history.

(56) References Cited

U.S. PATENT DOCUMENTS

| | | | |
|---|---|---|---|
| 4,244,940 A | 1/1981 | Jeong et al. |
| 4,513,006 A | 4/1985 | Maryanoff et al. |
| 4,659,516 A | 4/1987 | Bowler et al. |
| 4,792,569 A | 12/1988 | Maryanoff et al. |
| 5,001,234 A | 3/1991 | Bundy et al. |
| 5,025,031 A | 6/1991 | Lo et al. |
| 5,116,828 A | 5/1992 | Miura et al. |
| 5,705,495 A | 1/1998 | Schwarz et al. |
| 5,866,603 A | 2/1999 | Li et al. |
| 6,339,079 B1 | 1/2002 | Kasch |
| 6,355,666 B1 | 3/2002 | Lai et al. |
| 6,436,917 B1 | 8/2002 | Droescher et al. |
| 6,583,130 B1 | 6/2003 | Schwarz |
| 6,713,487 B2 | 3/2004 | Yu et al. |
| 6,841,548 B2 | 1/2005 | Schwarz |
| 6,956,031 B2 | 10/2005 | Hillisch |
| 6,958,327 B1 | 10/2005 | Hillisch et al. |
| 2003/0100544 A1 | 5/2003 | Scherlitz-Hofmann et al. |
| 2004/0014781 A1 | 1/2004 | Elger |
| 2004/0087565 A1 | 5/2004 | Kosemund et al. |
| 2004/0102630 A1 | 5/2004 | Brumby et al. |
| 2005/0277625 A1 | 12/2005 | Wyrwa et al. |
| 2005/0288267 A1 | 12/2005 | Wyrwa et al. |
| 2007/0123500 A1 | 5/2007 | Mueller |
| 2007/0135375 A1 | 6/2007 | Wyrwa |
| 2007/0135399 A1 | 6/2007 | Wyrwa |
| 2007/0197488 A1 | 8/2007 | Peters |

FOREIGN PATENT DOCUMENTS

| | | |
|---|---|---|
| DE | 12 03 042 | 10/1965 |
| DE | 4236237 A1 | 4/1994 |
| DE | 197 12 488 A1 | 3/1997 |
| EP | 0 003 383 A2 | 8/1979 |
| EP | 0 424 954 A | 5/1991 |
| WO | WO 93/05064 | 3/1993 |
| WO | WO 94/14827 | 7/1994 |
| WO | WO 94/26702 | 11/1994 |
| WO | WO 96/05216 | 2/1996 |
| WO | WO 97/14712 | 4/1997 |
| WO | WO 00/06475 | 2/2000 |
| WO | WO 01/51055 | 7/2001 |
| WO | WO 01/77139 A1 | 10/2001 |
| WO | WO 01/91797 A | 12/2001 |
| WO | WO 03/104253 A2 | 12/2003 |
| WO | WO 2005/051401 A2 | 6/2005 |
| WO | WO 2005/113574 A1 | 12/2005 |
| WO | WO 2005/113575 A | 12/2005 |
| WO | WO 2005/113576 A | 12/2005 |
| WO | WO 2006/108879 A | 10/2006 |

OTHER PUBLICATIONS

Williams J et al: "The oral administration of polysorbate 80 to the immature female rat does not increase uterine weight." Toxicology Letters. Mar. 14, 1997.
Purohit A et al: "Steroid sulphatase inhibitors for breast cancer therapy." The Journal of Steroid Biochemistry and Molecular Biology. Sep. 2003.

(Continued)

*Primary Examiner*—Barbara P Badio
(74) *Attorney, Agent, or Firm*—Millen, White, Zelano & Branigan, P.C.

(57) ABSTRACT

The invention relates to estradiol prodrugs of general formula (I), in which group Z is bonded to the steroid,

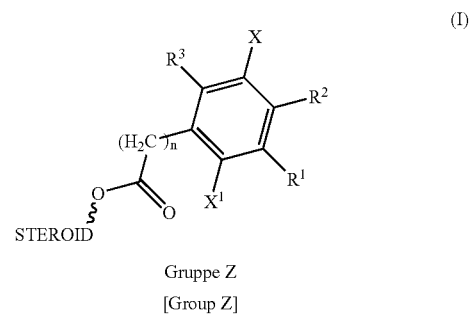

process for their production, pharmaceutical compositions that contain these compounds, as well as their use for the production of pharmaceutical agents with estrogenic action.

26 Claims, 2 Drawing Sheets

OTHER PUBLICATIONS

Elger W et al: "Estrogen sulfamates: a new approach to oral estrogen therapy." Reproduction, Fertility and Development. 2001.

Chander Surinder K et al: "The role of steroid sulphatase in regulating the oestrogenicity of oestrogen sulphamates." Biochemical and Biophysical Research Communications. Sep. 10, 2004.

Chandler, Surinder K. et al., "The Role of Steroid Sulphatase in Regulating the Oestrogenicity of Estrogen Sulphamates," Biochemical and Biophysical Research Communications, 2004, pp. 217-222, vol. 322, Elsevier, Inc.

Elger, W. et al., "Estrogen Sulfamates: a New Approach to Oral Estrogen Therapy," Reprod. Fertil. Dev., 2001, pp. 297-305, vol. 13, CSIRO Publishing, Australia.

Purohit, A. et al., "Steriod Sulphatase Inhibitors for Breast Cancer Therapy," Journal of Steriod Biochemistry & Molecular Biology, 2003, pp. 423-432, vol. 86, Elsevier Ltd.

Williams, J. et al., "The Oral Administration of Polysorbate 80 to the Immature Female Rat Does Not Increase Uterine Weight," Toxicology Letters, 1997, pp. 19-24, vol. 91, Elsevier Science Ireland Ltd.

A. Purohit et al. Steroid Sulphatase Inhibitors for Breast Cancer Therapy, Journal of Steroid Biochemistry & Molecular Biology, vol. 86, (2003) pp. 423-432.

W. Elger et al. Estrogen Sulfamates: A New Approach to Oral Estrogen Therapy, Reproduction, Fertility and Development, vol. 13, (2001) pp. 297-305.

Claude A. Quesnelle et al., "Sordaricin Antifungal Agents," Bioorganic and Medicinal Chemistry Letters, Feb. 10, 2003, vol. 13, No. 3, pp. 519-524, XP002432733, ISSN:0960-894X.

Carolyn H. Kruse et al., "Synthesis and Evaluation of Multisubstrate Inhibitors of an Oncogene-Encoded Tyrosine-Specific Protein Kinase," J. Med. Chem., Sep. 1998, vol. 31, No. 9, pp. 1762-1767, XP002432734, ISSN: 0022-2623.

Sally-Ann Poulsen et al., "Synthesis and Structure-activity relationships of novel benze sulfonamides with potent binding affinity for bovine carbonic anhydrase II," Oct. 6, 2005, pp. 5429-5433, XP005136456, ISSN: 0960-994X.

Takuo Aoyama et al., "Synthesis and Structure-Activity Study of Protease Inhibitors," Chemical and Pharmaceutical Bulletin, Pharmaceutical Society of Japan, 1985, vol. 33, No. 4, pp. 1458-1471, XP002110067, ISSN: 0009-2363.

Gomes J R B et al., "Gas-phase acidity of sulfonamides: implications for reactivity and prodrug design", Tetrahedron, Mar. 7, 2005, 2705-2712, vol. 61, Nbr. 10, Elsevier Science Publishers, Amsterdam.

International Search Report for related international application PCT/EP2006/011727, filed Nov. 27, 2006; Search conducted Mar. 27, 2007.

"Synthesis of estrogen sulfamates: Compounds with a novel endocrinological profile", Sigfrid Schwarz et al., Steroids, 1996, vol. 61, December, pp. 710-717.

Jahrgang 30, Hefte 1-12 - 1975 - Die Pharmazie, Steroide, S. Schwarz et al., pp. 17-21.

Chemische Berichte, Rolf Appel und Serner Senkpiel, pp. 1102-1105, 1959.

Annalen Der Chemie, Herstellung and Reaktionen von N-Monoalkyl-amidosulfonylchloriden, von Gunther Weiβ et al., pp. 40-51.

"X-ray Crystal Structure and Mechanism of Action of Oestrone 3-O-Sulphamate, a Synthetic Active Site-directed Inhibitor of Oestrone Sulphatase", Gary J. Williams et al., Pharmaceutical Sciences 1996, pp. 11-16.

"Development of an Oral Formulation of Oestrone 3-O-Sulphamate, a Potent Sulphatase Inhibitor", Ulrike G. Sahm et al., Pharmaceutical Sciences 1996, pp. 17-20.

17β-Hydroxy-11α-(3'-sulfanylpropyl)oxy-estra-1,3,5(10)-trien-3-yl sulfamate - a novel hapten structure: Toward the development of a specific enzyme immunoassay (EIA) for estra- 1,3,5(10)-triene-3-yl sulfamates, Steroids 64 (1999), pp. 460-471.

J. Med Chem. Jun. 23, 1995;38(13):2286-91 - Secondary Interactions significantly removed from the sulfonamide binding pocket of carbonic anhydrase II influence inhibitor binding constants - Boriack PA, Christianson DW, Kingery-Wood J., Whitesides GM. Abstract only.

Blood Carbonic Anhydrase Activity In Anemia, With A Note On Polycythemia Vera, H.D. Lewis et al., pp. 442-454. date needed.

Enzymatic Conjugation of Erythrocyte Glutathione With 1-Chloro-2,4-Dinitrobenzene: The Fate of Glutathione Conjugate in Erythrocytes and the Effect of Glutathione Depletion on Hemoglobin, Yogesh C. Awasthi et al., pp. 733-738. 1981.

J. Med Chem. Aug. 7, 1992;35(16):3027-33 - Thieno[2,3-b]furan-2-sulfonamides as topical carbonic anhydrase inhibitors - Hartman GD et al. Abstract only.

J Biol Chem. Dec. 15, 1993;268(35):26233-9 - A new class of carbonic anhydrase inhibitor - Maren TH et al. Abstract only.

Int J. Biol Macromol. Apr. 1993;15(2):97-100 - Refined structure of the aminobenzolamide complex of human carbonic anhydrase III - Vidgren J et al. Abstract only.

J Med Chem. Jan. 21, 1994;37(2):240-7 - 3-substituted thieno[2,3-b][1,4]thiazine-6-sulfonamides. A novel class of topically active carbonic anhydrase inhibitors - Hunt CA et al. Abstract only.

Mol Pharmacol. Sep. 1995;48(3):486-91 - The effect of temperature on the binding of sulfonamides to carbonic anhydrase isoenzymes I, II, and IV - Conroy CW et al. Abstract only.

Biorg Med Chem. Mar. 1997;5(3):515-8 - Synthesis and investigation of inhibition effects of new carbonic anhydrase inhibitors - Arslan O. Kufrevioglu et al. Abstract only.

Protein Sci. Dec. 1998;7(12):2483-9 - Structural analysis of inhibitor binding to human carbonic anhydrase II - Boriack-Sjodin et al. Abstract only.

Bioorg Med Chem. Nov. 1999;7(11):2397-406 - carbonic anhydrase inhibitors: synthesis of water-soluble, topically effective intraocular pressure lowering aromatic-heterocyclic sulfonamides containing 8-quinoline-sulfonyl moieties: is the tail more important than the ring? - Borras J. et al. Abstract only.

Bioorg Med Chem. May 2000;8(5):957-75 - 2H-Thieno[3,2-e]- and [2,3-e]-1,2-thiazine-6-sulfonamide 1,1-dioxides as occular hypotensive agents: synthesis, carbonic anhydrase inhibition and evaluation in the rabbit - Chen HH et al. Abstract only.

Brinzolamide, Ophthalmic Suspension 1%, Azopt - Summary Basis Of Approval Equivalent, Alcon Laboratories, Inc., pp. 1-23. 2006.

AZOPT (brinzolamide ophthaimic suspension) 1%, Alcon Laboratories, Inc., pp. 1-3. 2006.

Annex I Summary of Product Characteristics pp. 1-22. 2006.

Barth A et al.: "Influence Of Subchronic Administration Of Oestradiol, Ethinyloestradiol and Oestradiol Sulphamate On Bile Flow, Bile Acid Excretion, And Liver And Biliary Glutathione Status In Rats", Archives of Toxicology, Springer Verlag, DE, vol. 71, No. 7, 1997, pp. 443-449, XP000986430, ISSN 0340-5761.

Elger W et al.: "Sulfamates Of Various Estrogens Are Prodrugs With Increased Systemic And Reduced Hepatic Estrogenicity At Oral Application", Journal of Steroid Biochemistry and Molecular Biology, Elsevier Science Ltd., Oxford, GB, vol. 55, No. 3/4, 1995, 1995, pp. 395-403, XP000518892, ISSN 0960-0760.

Maryanoff B E et al.: "Anticonvulsant Sugar Sulfamates. Potent Cyclic Sulfate And Cyclic Sulfite Analogues Of Topiramate", Bioorganic & Medicinal Chemistry Letters, Oxford, GB, vol. 3, No. 12, 1993, pp. 2653-2656, XP000914306, ISSN 0960-894X.

Office Action dated Mar. 18, 2008 in U.S. Appl. No. 11/605,473.

Office Action dated Dec. 27, 2007 in U.S. Appl. No. 11/605,472.

Office Action dated Feb. 29, 2008 in U.S. Appl. No. 11/604,891.

ET 03.14 Examination in the Uterus Growth Test After Peroral Administration Over 3 Days in OVX Rats μg/Animal/Day

ESTRADIOL PRODRUGS

This application claims the benefit of the filing date of U.S. Provisional Application Ser. No. 60/572,964 filed May 21, 2004 which is incorporated by reference herein.

The invention relates to estradiol prodrugs of general formula I,

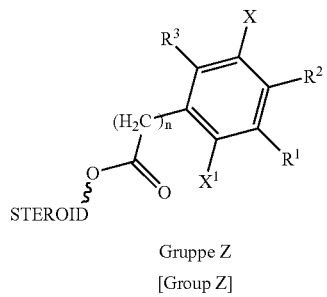

Gruppe Z

[Group Z]

a process for their production, pharmaceutical compositions that contain these compounds, and their use for the production of pharmaceutical agents with estrogenic action.

Estrogens play an important role in the organism in both sexes. Estrogens in the maturing organism are involved in the imprinting of sex characteristics. In both sexes, estrogens control the changes in the organism during sexual maturation, such as growth spurts and then the completion of bone growth. In all phases of life, estrogens play a central role in bone metabolism in both sexes[1]. Its loss results in the degradation of bone substance and involves the risk of an elevated brittleness of the bone.

In women, the estrogens that are secreted by the ovary predominate in the organism. In pregnancy, the placenta forms large amounts of estrogen. In men, estrogens are produced primarily "peripherally" by the aromatization of testosterone or the adrenal androgens in various effector organs, such as the central nervous system (CNS), the bones or the intestinal epithelium. This adaptation makes possible physiological estrogen effects in men at very low estradiol levels in the blood. In men and women with a genetic defect of the aromatase or the estrogen receptor, the bones are severely disrupted relative to growth and development[2].

In oral administration, the natural estrogens have a low oral bioavailability[3]. With respect to the improvement of oral bioavailabilhty, natural estrogens were modified. Conventional chemically modified estrogens with improved bioavailability, e.g., the ethinyl estradiol, often have another drawback, namely a significantly increased estrogenic action in the liver[4].

This hepatic estrogeneity relates to a number of functions, such as transport proteins, lipometabolism, blood pressure regulation and clotting factors[5]. Also, the especially important secretion of IGF-I[6] for the preservation of muscles and bones is negatively affected by hepatic estrogenic actions.

Steroidally active compounds that are bonded to erythrocytes via a group —$SO_2NR^1R^2$ and that accumulate there are known from DE 100 27 887.6 A1. The concentration ratio of the compounds between erythrocytes and plasma is 10-1000, preferably 30-1000, so that it is possible to speak of a depot formation in the erythrocytes. By the strong binding of the compounds to the erythrocytes, metabolization while passing through the liver is avoided. Disadvantageously, despite reduced metabolization with the indicated dosages, no therapy-relevant active ingredient levels are provided.

It is the object of the invention to prepare new steroidal compounds with estrogenic action that are orally available and, in comparison to the prior art, also to ensure a therapy-relevant active ingredient level even at a lower dosage.

This object is achieved by estradiol prodrugs of general formula (I), in which group Z is bonded-to the steroid that is to be released,

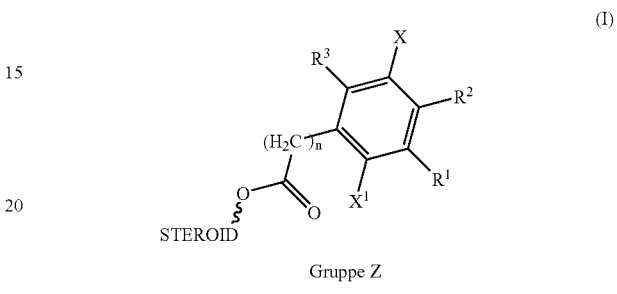

Gruppe Z

[Group Z]

in which n is a number 0-4, $R^1$ is a radical —$SO_2NH_2$ or —$NHSO_2NH_2$, whereby $R^2$, $R^3$ and X, $X^1$ stand for a hydrogen atom, a halogen atom, a nitrile group, a nitro group, a $C_{1-5}$-alkyl group, a $C_pF_{2p+1}$ group with p=1-3, a group OC(O)—$R^{20}$, COO$R^{20}$, O$R^{20}$, C(O)NH$R^{20}$ or OC(O)NH—$R^{21}$, whereby $R^{20}$, $R^{21}$ and $R^{22}$ are a $C_{1-5}$-alkyl group, a $C_{3-8}$-cycloalkyl group, an aryl group, a $C_{1-4}$-alkylene aryl group, a $C_{1-4}$-alkylene-$C_{3-8}$-cycloalkyl group or a $C_{3-8}$-cycloalkylene-$C_{1-4}$-alkyl group, and $R^{20}$ in addition can mean a hydrogen, or $R^2$ is a radical —$SO_2NTH_2$ or —$NHSO_2NH_2$, whereby $R^2$, $R^3$ and X, $X^1$ stand for a hydrogen atom, a halogen atom, a nitrile group, a nitro group, a $C_{1-5}$-alkyl group, a $C_pF_{2p+1}$ group with p=1-3 a group OC(O)—$R^{20}$, COO$R^{20}$, O$R^{20}$, C(O)NH$R^{20}$ or OC(O)NH—$R^{21}$, whereby $R^{20}$, $R^{21}$ and $R^{22}$ are a $C_{1-5}$-alkyl group, a $C_{3-8}$-cycloalkyl group, an aryl group, a $C_{1-4}$-alkylene aryl group, a $C_{1-4}$-alkylene-$C_{3-8}$-cycloalkyl group or a $C_{3-8}$-cycloalkylene-$C_{1-4}$-alkyl group, and $R^{20}$ in addition can mean a hydrogen, or $R^3$ is a radical —$SO_2NH_2$ or —$NHSO_2NH_2$, whereby $R^2$, $R^3$ and X, $X^1$ stand for a hydrogen atom, a halogen atom, a nitrile group, a nitro group, a $C_{1-5}$-alkyl group, a $C_pF_{2p+1}$ group with p=1-3, a group OC(O)—$R^{20}$, COO$R^{20}$, O$R^{20}$, C(O)NH$R^{20}$ or OC(O)NH—$R^{21}$, whereby $R^{20}$, $R^{21}$ and $R^{22}$ are a $C_{1-5}$-alkyl group, a $C_{3-8}$-cycloalkyl group, an aryl group, a $C_{1-4}$-alkylene aryl group, a $C_{1-4}$-alkylene-$C_{3-8}$-cycloalkyl group or a $C_{3-8}$-cycloalkylene-$C_{1-4}$-alkyl group, and $R^{20}$ in addition can mean a hydrogen, and STEROID stands for a steroidal ABCD-ring system of general partial formulas (II A) and (II B),

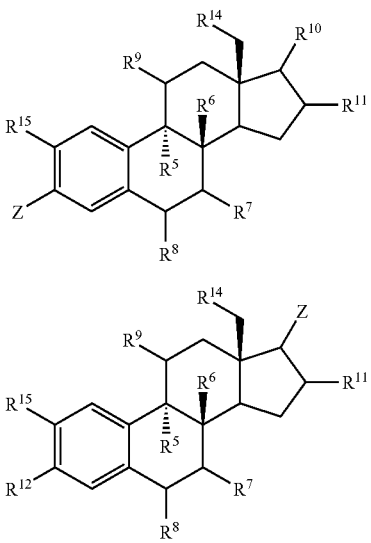

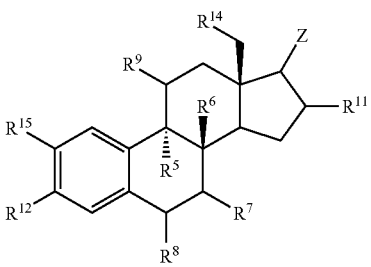

whereby
- $R^5$, $R^6$ and $R^8$ in each case represent a hydrogen atom, and $R^7$ represents a hydrogen atom, a methyl group or an ethyl group, or
- $R^5 \div R^6$, $R^7 \div R^8$ or $R^6 \div R^7$ together represent a double bond.
- $R^9$ represents a hydrogen atom, a halogen atom, a hydroxy group, a methoxy group, a group OC(O)—$R^{20}$ a methyl or ethyl group,
- $R^{10}$ represents a hydroxy groups a methoxy group, a tri($C_{1-6}$-alkyl)silyloxy group, a group OC(O)—$R^{20}$, a $C_{2-5}$-heterocycloalkyloxy group or a group Z,
- $R^{11}$ represents a hydrogen atom or a halogen atom,
- $R^{12}$ represents a hydroxy group, a methoxy group, a tri($C_1$-$C_6$-alkyl)silyloxy group, a group OC(O)—$R^{20}$, a $C_{2-5}$-heterocycloalkyloxy group or a group Z,
- $R^{14}$ represents a hydrogen atom, a methyl group, or an ethyl group,
- $R^{15}$ represents a hydrogen atom, a hydroxy group, a methoxy group, an ethoxy group, a tri($C_{1-6}$-alkyl)silyloxy group, a group OC(O)—$R^{20}$ or a $C_{2-5}$-heterocycloalkyloxy group, and their pharmaceutically acceptable salts.

The compounds according to the invention have estrogenic activity.

In the context of this invention, "$C_{1-5}$-alkyl group" is defined as a branched or straight-chain alkyl radical with 1 to 5 carbon atoms, which can be substituted by, e.g., halogen atoms, hydroxy groups, or nitrile groups. As examples, a methyl, ethyl, n-propyl, i-propyl, n-butyl, i-butyl, tert-butyl or n-pentyl group can be mentioned.

According to the invention, the above-mentioned "$C_{3-8}$-cycloalkyl group" means a monocyclic or bicyclic group, which can be substituted by, for example, halogen atoms, hydroxy groups, or nitrile groups, such as, for example, a cyclopropyl, cyclobutyl, cyclopentyl, cyclohexyl or a hydroxycyclohexyl group.

In the context of this application, the term "aryl group" is defined as a substituted or unsubstituted aryl radical with 6 to 15 carbon atoms, for example a phenyl group, a substituted phenyl group, such as a halophenyl group, or a nitrophenyl group, or a naphthyl group.

In the context of this application, the term "$C_{1-4}$-alkylene aryl group" is defined as a disubstituted alkyl radical that is substituted at least with an aryl radical. Both radicals together have 7 to 15 carbon atoms, whereby the group can carry additional substituents, such as, for example, a halogen atom. Examples are a benzyl group or a halobenzyl group.

In the context of this application, the term "$C_{1-4}$-alkylene-$C_{3-8}$-cycloalkyl group" is defined as a disubstituted alkyl radical that is substituted at least with a $C_{3-8}$-cycloalkyl radical. Both radicals together exhibit 7 to 15 carbon atoms, whereby the group can carry additional substituents, such as, for example, a halogen atom. Examples are a cyclopentylethyl, cyclohexylmethyl or cyclohexylethyl group.

In the context of this application, the term "$C_{3-8}$-cycloalkylene-$C_{1-4}$-alkyl group" is defined as a disubstituted $C_{3-8}$-cycloalkylene radical that is substituted at least with a $C_{1-4}$-alkyl radical. Both radicals together exhibit 7 to 15 carbon atoms, whereby the group can carry additional substituents, such as, for example, a halogen atom. Examples are a propylcyclohexyl group or a butylcyclohexyl group.

According to this invention, the term "$C_pF_{2p+1}$-group" is defined as a perfluorinated alkyl radical, such as, for example, a trifluoromethyl radical and a pentafluoroethyl radical.

The term tri($C_{1-6}$-alkyl)silyloxy group is defined as, for example, a trimethylsilyloxy group, a triisopropylsilyloxy group, a thexyldimethylsilyloxy group or a tert-butyldimethylsilyloxy group.

Within the scope of the invention, the term "$C_{2-5}$-heterocycloalkyloxy group" is defined as a $C_{1-5}$-heterocycloalkyloxy group with a nitrogen atom or an oxygen atom as a heteroatom, whereby the binding of the $C_{1-5}$-heterocycloalkyloxy, group is carried out via the oxygen atom in 2-, 3- or 4-position. An example of this is the perhydropyranoxy group.

Within the scope of this invention, the term "halogen atom" is defined as a fluorine, chlorine, bromine or iodine atom; a fluorine, chlorine or bromine atom is preferred.

The number "n" is preferably 0, and 2, and especially preferably 0.

It is preferred that $R^1$ represent the radical —$SO_2NH_2$ or —$NHSO_2NH_2$, whereby the radical —$SO_2NH_2$ is especially preferred. The above-mentioned radicals thus are found in m-position of group Z in relation to the ester group, via which group Z is bonded to the steroid.

- $R^1$ preferably means a group —$SO_2NH_2$, whereby $R^2$, $R^3$, $X^1$ and X preferably are a hydrogen atom, a fluorine atom, a chlorine atom, a hydroxy group or a methoxy group, or
- $R^2$ preferably means a group —$SO_2NH_2$, whereby $R^1$, $R^3$, $X^1$ and X preferably are a hydrogen atom, a fluorine atom, a chlorine atom, a hydroxy group or a methoxy group, or
- $R^3$ preferably means a group —$SO_2NH_2$, whereby $R^1$, $R^2$, $X^1$ and X preferably are a hydrogen atom, a fluorine atom, a chlorine atom, a hydroxy group or a methoxy group.

$R^5$, $R^6$, $R^7$ and $R^8$ are preferably in each case a hydrogen atom.

$R^9$ and $R^{11}$ are preferably and independently of one another a hydrogen atom or a fluorine atom.

$R^{10}$ and $R^{12}$ are preferably a hydroxy group, a methoxy group, a trimethylsilyloxy radical, a tert-butyldimethylsilyloxy radical, a benzoate radical, an acetate radical, a propionate radical, a valerate radical, a butciclate radical (i.e., a (trans-4-n-butyl) cyclohexylcarboxylate radical or a cyclopentylpropionate radical, or the group Z. In each case, a hydroxy group is especially preferred.

R$^{14}$ is preferably a hydrogen atom.

R$^{15}$ is preferably a hydrogen atom, a methoxy group or an ethoxy group.

Radicals R$^9$ in 11-position, R$^7$ in 17-position, R$^{10}$ in 17-position, and R$^{11}$ in 16-position can be arranged both in α-position and in β-position.

Especially preferred compounds or estradiol prodrugs are cited below:

1) 3-Hydroxyestra-1,3,5(10)-trien-17β-yl 3'-sulfamoylbenzoate (9),
2) 3-Acetoxyestra-1,3,5(10)-trien-17β-yl 3'-sulfamoylbenzoate,
3) 3-tert.-Butyldimethylsilyloxyestra-1,3,5(10)-trien-17β-yl 3'-sulfamoylbenzoate (10),
4) 3-Hydroxyestra-1,3,5(10)-trien-17β-yl 2'-chloro-5'-sulfamoylbenzoate (21),
5) 3-Hydroxyestra-1,3,5(10)-trien-17β-yl 3'-sulfamoyl-4'-chloro-benzoate (3),
6) 3-Hydroxyestra-1,3,5(10)-trien-17β-yl 2',4'-dichloro-5'-sulfamoylbenzoate (7),
7) 3-Hydroxyestra-1,3,5(10)-trien-17β-yl 2'-chloro-4'-fluoro-5'-sulfamoylbenzoate (5),
8) 3-Hydroxyestra-1,3,5(10)-trien-17β-yl 2'-methoxy-5'-sulfamoylbenzoate (12),
9) 3-tert.-Butyldimethylsilyloxyestra-1,3,5(10)-trien-17β-yl 2'-methoxy-5'-sulfamoylbenzoate
10) 3-Hydroxyestra-1,3,5(10)-trien-17-yl 2',3'-dimethoxy-5'-sulfamoylbenzoate (19),
11) 3-Hydroxyestra-1,3,5(10)-trien-17β-yl 4'-sulfamoylbenzoate (1),
12) 2-Methoxy-3-hydroxyestra-1,3,5(10)-trien-17β-yl 3'-sulfamoylbenzoate,
13) 2-Methoxy-3-hydroxyestra-1,3,5(10)-trien-17β-yl 2'-chloro-5'-sulfamoylbenzoate,
14) 2-Methoxy-3-hydroxyestra-1,3,5(10)-trien-17β-yl 3'-sulfamoyl-4'-chloro-benzoate,
15) 2-Methoxy-3-hydroxyestra-1,3,5(10)-trien-17β-yl 2',4'-dichloro-5'-sulfamoyl-benzoate,
16) 2-Methoxy-3-hydroxyestra-1,3,5(10)-trien-17β-yl 2'-chloro-4'-fluoro-5'-sulfamoylbenzoate,
17) 2-Methoxy-3-hydroxyestra-1,3,5(10)-trien-17β-yl 4'-sulfamoylbenzoate,
18) 2-Methoxy-3-hydroxyestra-1,3,5(10)-trien-17β-yl 4'-sulfamatobenzoate,
19) 3-Benzoyloxyestra-1,3,5(10)-trien-17β-yl 3'-sulfamoylbenzoate (14),
20) 17β-(n-Pentanoyloxy)estra-1,3,5(10)-trien-3-yl 3'-sulfamoylbenzoate (15),
21) 17β-Benzoyloxyestra-1,3,5(10)-trien-3-yl 3'-sulfamoylbenzoate (16),
22) 17β-Hydroxyestra-1,3,5(10)-trien-3-yl 4'-sulfamoylbenzoate (17),
23) 17β-Hydroxyestra-1,3,5(10)-trien-3-yl 2',3'-dichloro-5'-sulfamoylbenzoate (24),
24) 17β-Hydroxyestra-1,3,5(10)-trien-3-yl 2'-chloro-4'-fluoro-5'-sulfamoylbenzoate (23),
25) 3-Methoxyestra-1,3,5(10)-trien-17β-yl 3'-sulfamoylbenzoate (11),
26) 3-Hydroxyestra-1,3,5(10)-trien-17β-yl 2'-sulfamoylbenzoate (25),
27) 3-Benzoyloxyestra-1,3,5(10)-trien-17β-yl 2'-sulfamoylbenzoate (26),
28) 2-Methoxy-3-hydroxyestra-1,3,5(10)-trien-17β-yl 2',3'-dimethoxy-5'-sulfamoylbenzoate,
29) Estra-1,3,5(10)-trien-3,17β-diyl bis(3'-sulfamoylbenzoate) (27)
30) 2-Ethoxy-3-hydroxyestra-1,3,5(10)-trien-17β-yl 3'-sulfamoylbenzoate,
31) 2-Ethoxy-3-hydroxyestra-1,3,5(10)-trien-17β-yl 2'-chloro-5'-sulfamoylbenzoate,
32) 2-Ethoxy-3-hydroxyestra-1,3,5(10)-trien-17β-yl 3'-sulfamoyl-4'-chloro-benzoate,
33) 2-Ethoxy-3-hydroxyestra-1,3,5(10)-trien-17β-yl 2',4'-dichloro-5'-sulfamoyl-benzoate,
34) 2-Ethoxy-3-hydroxyestra-1,3,5(10)-trien-17β-yl 2'-chloro-4'-fluoro-5'-sulfamoylbenzoate,
35) 2-Ethoxy-3-hydroxyestra-1,3,5(10)-trien-17β-yl 4'-sulfamoylbenzoate,
36) 2-Ethoxy-3-hydroxyestra-1,3,5(10)-trien-17β-yl 4'-sulfamatobenzoate,
37) 2-Ethoxy-3-hydroxyestra-1,3,5(10)-trien-17β-yl 2',3'-dimethoxy-5'-sulfamoylbenzoate,
38) 3-tert.-Butyldimethylsilyloxyestra-1,3,5(10)-trien-17β-yl 2'-chloro-4'-sulfamoylbenzoate (28)
39) 3-Hydroxyestra-1,3,5(10)-trien-17β-yl 2'-chloro-4'-sulfamoylbenzoate (29)

For the formation of pharmaceutically acceptable salts of the compounds of general formula I according to the invention, i.a., hydrochloric acid, hydrobromic acid, sulfuric acid and phosphoric acid are considered as inorganic acids, and, i.a., acetic acid, propionic acid, maleic acid, fumaric acid, succinic acid, benzoic acid, ascorbic acid, oxalic acid, salicylic acid, tartaric acid, citric acid, lactic acid, malic acid, mandelic acid, cinnamic acid and methanesulfonic acid are considered as organic acids.

The compounds according to the invention have estrogenic activity in the case of oral administration, whereby hepatic effects, unlike in conventional estrogens, are avoided to a very large extent. The compounds according to the invention do not themselves bind to the estrogen receptor, rather the therapeutically relevant steroid is released from the latter by ester cleavage.

In-Vivo Tests

Surprisingly and unexpectedly, a very strong increase of "mother estrogen," e.g., in compound 9 of estradiol, was found in in-vivo experiments in rats for the compounds according to the invention in the case of oral administration, as it is not found in other esters, for example of estradiol. The relevance of this finding is explained by a strong action of the substances according to the invention on the uterus growth in ovariectomized rats.

Principle of the Test and Test Description:

Adult Wistar rats were ovariectomized 14 days after this operation for the study of the substances according to the invention. A treatment extended over 3 days (days 1-3); on day 4 after the animals were sacrificed, the recovery of plasma for hormone-analytical and clinical-chemical determinations and the determination of uterus weights were carried out. In satellite tests, correspondingly conditioned animals were sacrificed and samples were taken of their blood after one-time treatment and at other times (see Table 1 for determining estradiol and estrone in the plasma).

TABLE 1

Increase of estradiol(E2) and estrone (E1) levels in the plasma of rats after one-time oral administration of compounds 9 and compound 1 (0.05 mg/animal): Significantly larger increase of E2 than of E1 in pharmacodynamically relevant values

| Animal No. | Time (minutes) | Compound 9* | | Compound 1* | |
|---|---|---|---|---|---|
| | | E1 (pg/ml) | E2 (pg/ml) | E1 (pg/ml) | E2 (pg/ml) |
| 3516 | 15 | 87.48 | 899.98 | | |
| | 60 | 141.23 | 782.40 | | |
| | 120 | 41.82 | 178.45 | | |
| | 360 | <15 | 25.95 | | |
| 3519 | 10 | | | 73.52 | 523.94 |
| | 45 | | | 54.81 | 270.34 |
| | 120 | | | <15 | 46.88 |
| | 480 | | | <15 | 69.77 |

*$^3$H Compound

In FIG. 1, the induction of uterus growth in ovariectomized rats is depicted. The treatment is carried out orally from day 1 to the 3$^{rd}$ day, and then the autopsy is carried out on the 4$^{th}$ day. A maximum uterus growth predominantly at 30 µg/animal/day is shown.

Surprisingly and unexpectedly, an estrogenic activity in the uterus, enhanced in comparison to estradiol, was found, moreover, e.g., for compound 9. In the case of oral administration in ovariectomized rats, substances according to the invention have a significantly stronger action on the uterus than conventional estrogens.

While even at low dosages that do not even affect the uterus ethinyl estradiol leads to a significant increase in angiotensinogen, no change or considerably smaller changes in markers of hepatic estrogenic action were found with dosages of substances according to the invention that are fully effective in the uterus.

FIG. 2 shows estrogenic activity (uterus growth) and liver estrogeneity (marker: angiotensinogen (antiotensin 1 is produced by enzymatic conversion from angiotensinogen by the addition of renin to the sample) of compound I in comparison to the standard estrogen ethinyl estradiol (EE). In this case, an increase of angiotensin 1 means a more significant, undesirable impact on the liver.

The compound according to the invention has a superior action on the uterus growth, a much lesser action on estrogen-modulated liver functions than the EE.

Vitro Tests:

Studies with respect to bonds of m-substituted compounds 9 and 7 and the p-substituted compound 1 to erythrocytes were also surprising. For the m-substituted derivatives, weaker bonds were detected. Compound 1, however, shows a very strong bond.

In this case, however, it was unexpected that, e.g., m-substituted compound 9, despite lower binding strength to erythrocytes, has a higher oral availability and estrogeneity than the p-substituted compound. The data in Table 2 are to illustrate the binding to erythrocytes of selected compounds according to Formula I.

TABLE 2

Binding of Selected Compound to Erythrocytes

| Compound | RBA to Erythrocytes | Distribution Ratio of the Substance to Erythrocytes/Plasma |
|---|---|---|
| Estradiol-3-sulfamate | 100 | 49 |
| 1 | 32 | 7.7 |
| 9 | 0.18 | 4 |
| 7 | 0.40 | 5 |

Principle of the Test

The $SO_2$—$NTH_2$ group of the substances according to the invention can result in a concentration in erythrocytes by binding to carboanhydrases. The displacement of estradiol-3-sulfamate from the erythrocyte bond by test substances is measured.

Test preparation: Human blood is mixed with a mixture that consists of $^{14}$C-labeled and unlabeled estradiol sulfamate. The erythrocytes are saturated at the selected working point, and the distribution in plasma/erythrocytes is 40:60. A second blood sample is mixed with a mixture that consists of $^{14}$C-labeled estradiol sulfamate and unlabeled test substance. The relative binding affinity is calculated from the proportion of $^{14}$C-labeled estradiol sulfamate in plasma: higher proportion=strong displacement of $^{14}$C-estradiol sulfamate from the erythrocytes by the test substance=high binding affinity of the test substances to the erythrocytes.

Test Description

Determination of the substance concentration in the erythrocyte/plasma ratio (tracer use):

Fresh blood is incubated with a defined amount of tracer compound of compound 1 or 9. After the erythrocytes are separated, the measured radioactivity in the erythrocytes is put into a ratio with the measured radioactivity in the plasma.

Determination of the erythrocyte/plasma ratio (non-radioactive):

Freshly-obtained, heparinized blood is mixed with a defined amount of test substance. The concentration in the plasma obtained therefrom is measured. The erythrocyte/plasma ratio is calculated from the measured concentration of the total substance in the plasma and the concentration that is used.

In all cases a bond (inhibition) to the carboanhydrase (CA I) that is found in the erythrocytes nevertheless could be found (Table 3). It is therefore to be expected that the compounds according to the invention also have therapeutically relevant effects as carboanhydrase inhibitors. The bond to erythrocytes that is induced by the high affinity to carboanhydrases is important for properties as estrogen. This bond is essential for a reduced extraction of the orally administered substance in the first liver passage. High or low affinity to the erythrocytic carboanhydrases, faster or delayed release from this depot, and subsequent hydrolysis determine the therapeutic usability of the substances according to the invention.

It was found, unexpectedly, that the compounds according to the invention reach therapeutically relevant levels at lower dosages if the binding to the erythrocytes—unlike what is to be expected according to DE 100 27 887.6 A1—is less than 10. By the compounds according to the invention, the possibility is opened up that higher shorter-term or uniformly low and longer-lasting hormone levels can be achieved with the same absolute amount of substance administered. As a result, active strengths and durations of action are varied and make possible a therapy that is matched to the individual organism.

TABLE 3

IC$_{50}$ Inhibiting Values of Human Carboanhydrase I

| Inhibitor | CAI IC50 (nM) |
|---|---|
| Estradiol-3-sulfamate | 157 ± 10.6 |
| Compound 1 | 190 |
| Compound 9 | 380 |
| Compound 7 | 500 |
| Acetazolamide | 1200 |
| (of known CA inhibitors) | 1900[(8)] |

Principle of the Test and Test Description:

Carboanhydrases catalyze the $CO_2$ hydration.

Test preparation: A constant $CO_2$ stream is directed by a buffer that was mixed with carboanhydrase I. The time that is required to reduce the pH within defined limits is a measuring parameter. This parameter reflects the formation of $H_2CO_3$ in the medium. IC$_{50}$ inhibiting values are determined by test substances being pipetted into the test preparation. In the concentration areas that are examined, the test substances cause no inhibition to complete inhibition of the above-mentioned enzymes.

These test results open up many possible applications in the compounds of general formula (I) according to the invention or salts thereof in birth control and for hormone replacement therapy (HRT) in women or for the treatment of hormonally induced diseases in men and women, such as endometriosis, breast cancer, prostate cancer and hypogonadism.

Subjects of this invention are therefore also pharmaceutical compositions that contain at least one compound of general formula (I) or a corresponding salt, optionally together with at least one additional steroidal active ingredient, as well as optionally pharmaceutically compatible adjuvants and vehicles. As additional active ingredients for combination with the compounds of general formula (J) according to the invention, gestagens, antigestagens or mesoprogestins can be cited.

These pharmaceutical compositions and pharmaceutical agents can preferably be used for oral administration, but also for rectal, vaginal, subcutaneous, percutaneous, intravenous, transdermal or intramuscular administration. In addition to commonly used vehicles and/or diluents, they contain at least one compound of general formula I.

The pharmaceutical agents of the invention are produced with the commonly used solid or liquid vehicles or diluents and the commonly used pharmaceutical-technical adjuvants corresponding to the desired type of administration with a suitable dosage in a known way. The preferred preparations exist in a form for dispensing that is suitable for oral administration. Such forms for dispensing are, for example, tablets, film tablets, coated tablets, capsules, pills, powders, solutions or suspensions or else depot forms.

Of course, parenteral preparations such as injection solutions are also considered. In addition, for example, suppositories and agents for vaginal administration can also be mentioned as preparations.

Corresponding tablets can be obtained, for example, by mixing active ingredient with known adjuvants, for example inert diluents such as dextrose, sugar, sorbitol, mannitol, polyvinylpyrrolidone, explosives such as corn starch or alginic acid, binders such as starch or gelatins, lubricants such as magnesium stearate or talc and/or agents for achieving a depot effect such as carboxylpolyrnethylene, carboxyl methyl cellulose, cellulose acetate phthalate or polyvinyl acetate. The tablets can also consist of several layers.

Coating cores, which are produced analogously to the tablets, with agents that are commonly used in tablet coatings, for example polyvinyl pyrrolidone or shellac, gum Arabic, talc, titanium oxide or sugar, can accordingly produce coated tablets. In this case, the shell of the coated tablet can also consist of several layers, whereby the adjuvants that are mentioned above in the tablets can be used.

Solutions or suspensions with the compounds of general formula I according to the invention can contain additional taste-improving agents such as saccharine, cyclamate or sugar, as well as, e.g., flavoring substances such as vanilla or orange extract. In addition, they can contain suspending adjuvants such as sodium carboxy methyl cellulose or preservatives such as p-hydroxybenzoates.

The capsules that contain compounds of general formula I can be produced, for example, by the compound(s) of general formula I being mixed with an inert vehicle such as lactose or sorbitol and encapsulated in gelatin capsules.

Suitable suppositories can be produced, for example, by mixing with vehicles that are provided for this purpose, such as neutral fats or polyethylene glycol or derivatives thereof.

In the case of parenteral and oral administration, the compounds according to the invention have estrogenic activity; in this case, they exhibit properties that are pharmacokinetically improved compared to estradiol and 17α-ethinyl estradiol (EE) and that are based on a reduced hepatic extraction and more uniform and longer-lasting blood levels of the released estrogen. Also, the compounds according to the invention have estrogenic actions in the uterus that are enhanced compared to estradiol. In humans, the compounds according to the invention, unlike the oral therapy with estradiol or ethinyl estradiol, should not trigger any significant undesirable effects on estrogen-modulated functions in the liver.

The compounds according to the invention are suitable for all forms of an estrogen therapy and in this case can be used therapeutically by themselves or combined with a gestagen, antigestagen or mesoprogestin. In the combined oral contraception and analogous products for menopausal hormone substitution, they are also suitable as well for an estrogen treatment in the case of prostate cancer.

The substances according to the invention are prodrugs of natural estrogens. The substances according to the invention are preferably used for oral therapy. Compared to their "mother estrogens," the compounds according to the invention have a clearly increased oral bioavailability, an increased systemic, but generally reduced hepatic estrogeneity. By this dissociation of desirable and undesirable hormonal effects, simultaneously more therapeutically effective and, in comparison to the prior art, more compatible pharmaceutical agents are made possible.

In the case of oral therapy with natural estrogens (estradiol, estradiol valerate, estrone sulfate, conjugated estrogens), but also in that with estradiol sulfamate, high levels of estrone predominate in the blood. Unlike in menstruation, the concentrations of estradiol in the blood are lower than those of estrone. This is therefore disadvantageous, since estrone is a much less effective estrogen than estradiol. An advantage of the substances according to the invention in comparison to the prior art is the preferred release of the respective "mother estrogen," thus, for example, estradiol, equilin or equilenin.

The estradiol prodrugs according to the invention can be synthesized according to the examples below, whereby the latter are used for a more detailed explanation without limiting the invention.

General Synthesis Instructions

A) Coupling of the Steroidal Compound to Group Z

Variant 1

Reaction with Sulfamoylphenylcarboxylic Acids

An estrogen is dissolved in a base, such as, e.g., pyridine. Corresponding amounts of a sulfamoylphenylcarboxylic acid are added to the solution, then an acid, such as, e.g., p-toluenesulfonic acid, and finally a carbodiimides, such as, e.g., dicyclohexylcarbodiimide, are added. The reaction mixture is stirred until the reaction is completed. Then, water is added, and it is acidified with an acid, such as, e.g., 10% HCl. The precipitate is filtered off, washed with water and $NaHCO_3$ solution, and dried. The residue is extracted with an organic solvent, such as, e.g., ethyl acetate, the organic phase is washed and dried with a desiccant, such as, e.g., $MgSO_4$. After filtration, it is concentrated by evaporation and chromatographed on silica gel. Corresponding estrogen sulfamoyl benzoates are obtained.

Variant 2

Reaction with Sulfamoylphenylcarboxylic Acid Chlorides

An estrogen is dissolved in a base, such as, e.g., pyridine. The corresponding amount of a Sulfamoylphenylcarboxylic acid chloride is added to the solution. The reaction mixture is stirred until the reaction is completed. Then, water is added, and it is acidified with an acid, such as, e.g., 10% HCl. It is extracted with an organic solvent, such as, e.g., ethyl acetate, the organic phase is washed, and it is dried with a desiccant, such as, e.g., $MgSO_4$. After filtration, it is concentrated by evaporation and chromatographed on silica gel. Corresponding estrogen sulfamoyl benzoates are obtained.

Variant 3

Reaction with Chlorosulfonylphenylcarboxylic Acid Chlorides

An estrogen is dissolved in a base, such as. e.g., pyridine, and an organic solvent, such as, e.g., chloroform, and cooled. The corresponding amount of a chlorosulfonylphenyl-corboxylic acid chloride is added to the solution. The reaction mixture is stirred at room temperature until the reaction is completed. Then, the reaction mixture is stirred into concentrated ammonia solution. The mixture is concentrated by evaporation and acidified with an acid, such as, e.g., 10% HCl. The precipitate is suctioned off, washed with water, dried and chromatographed on silica gel. Corresponding estrogen sulfamoyl benzoates are obtained.

Variant 4

Reaction with 2-Sulfophenylcarboxylic Acid-Cyclo-Anhydride

An estrogen is dissolved in an organic solvent, such as, e.g., chloroform. After 2-sulfophenylcarboxylic acid-cyclo-anhydride is added, it is stirred at elevated temperatures under a cover gas. Then, it is cooled and mixed with a concentrated ammonia solution, such as, e.g., methanolic ammonia solution. The solvent is distilled off, and the residue is chromatographed on silica gel. 2'-Sulfophenylcarboxylic acid ester-ammonium salts of corresponding estrogens, which are dissolved under a cover gas in an organic solvent, such as, e.g., $CHCl_3$, are obtained. A corresponding amount of a chlorinating agent, such as, e.g., $PCl_5$ or $SOCl_2$, is added in portions. The reaction mixture is stirred optionally at elevated temperatures and then added briefly in concentrated $NH_3$ solution. The mixture is concentrated by evaporation, the precipitated substance is filtered off, washed with water, dried and chromatographed on silica gel. 2'-Sulfamoylphenylcarboxylic acid ester of corresponding estrogens is obtained.

Variant 5

Reaction to Form Sulfamides ($H_2SO_2NH$—)

The reaction to form the sulfonamides according to the invention is carried out according to methods that are known to one skilled in the art for their production starting from corresponding amines by means of sulfamide, sulfamoyl chloride or aminosulfonyl isocyanate (P. O. Burke et al., J. Chem. Soc. Perk. Trans 2, 1984, 1851; M. Preiss et al. Chem. Ber., 1978, 1915: C.-H. Lee et al., J. Org. Chem., 1990, 6104).

For example, a corresponding amino benzoate in an organic solvent, such as, e.g., toluene, is reacted in the presence of a base, such as, e.g., $NEt_3$, with sulfamoyl chloride at temperatures of 20-60° C. The reaction mixture is stirred until the reaction is completed. Then, water is added, the precipitate is filtered off, washed with water and $NaHCO_3$ solution and dried. The substance is purified by chromatography on silica gel. Corresponding estrogen sulfamoyl amino benzoates are obtained.

B) Examples of the Synthesis of Linkers (Z)

2-Chloro-4-sulfamoylbenzoic Acid

Stage 1

10 g of 2-chloro-toluene-4-sulfonic acid-Na-salt×$H_2O$ is added in 40 ml of thionyl chloride. After 5 ml of DMF is added, it is refluxed for 6 hours. The cold reaction mixture is added to 200 g of ice. The precipitated substance is washed with water and dried. 2-Chloro-toluene-4-sulfonic acid chloride is obtained.

$^1$H-NMR (DMSO-$d_6$): 2.32 (s, 3H, Me), 7.32-7.58 (m (superimposed), 3H, CH)

Stage 2

8 g of 2-chloro-toluene-4-sulfonic acid chloride is dissolved in 25 ml of $CHCl_3$ and slowly stirred into 100 ml of concentrated $NH_3$ solution. After 10 minutes of stirring at room temperature, the solution is concentrated by evaporation to one-half of its original volume. The substance is suctioned off, washed with water and dried. 2-Chloro-4-sulfamoyltoluene is obtained.

$^1$H-NMR (DMSO-$d_6$): 2.39 (s, 3H, Me), 7.44 (s, 2H, $NH_2$), 7.55-7.83 (m (superimposed), 3H, CH)

Stage 3

1.67 g of 2-chloro-4-sulfamoyltoluene is introduced into 70 ml of water. After 5 g of $KMnO_4$ and 0.5 ml of saturated $NaHCO_3$ solution are added, it is refluxed for 2 hours. After 2 ml of MeOH is added, the manganese dioxide that is produced is filtered off, and the solution is concentrated by evaporation to one-half of its original volume. After acidification with 10% HCl, the solution is cooled for 8 hours until crystallization is completed. Then, it is suctioned off, washed with water and dried. 2-Chloro-4-sulfamoylbenzoic acid is obtained.

$^1$H-NMR (DMSO-$d_6$): 7.66 (s, 2H, $NH_2$), 7.80-8.02 (m (superimposed), 3H, CH), 13.86 (s, 1H, COOH)

EXAMPLE 1

3-Hydroxyestra-1,3,5(10)-trien-17β-yl 4'-sulfamoylbenzoate (1)

Stage 1

3-tert.-Butyldimethylsilyloxyestra-1,3,5(10)-trien-17β-yl 4'-sulfamoylbenzoate (2)

Variant 1

1.0 g of 3-tert.-butyldimethylsilyloxyestra-1,3,5(10)-17β-ol is dissolved in 10 ml of pyridine. After 1.5 g of p-sulfamoylbenzoic acid, 200 mg of p-toluenesulfonic acid and 1.5 g of dicyclohexylcarbodiimide (DCC) are added, it is stirred for 48 hours at room temperature. Then, 20 ml of water and 50 ml of ethyl acetate are added. It is slightly acidified (pH=5) with 10% HCl. The precipitate is filtered off and rewashed with ethyl acetate. The organic phase is separated with 10% NaHCO$_3$ solution and washed with saturated NaCl solution, dried on MgSO$_4$, filtered, concentrated by evaporation and chromatographed on silica gel. 3-tert.-Butyldimethylsilyloxyestra-1,3,5(10)-17β-yl 4'-sulfamoylbenzoate is obtained.

Variant 2

1.0 g of 3-tert.-butyldimethylsilyloxyestra-1,3,5(10)-17β-ol is dissolved in 10 ml of pyridine. After 1.0 g of p-sulfamoylbenzoic acid chloride is added, it is stirred for 2 hours at room temperature. After 20 ml of water is added, it is slightly acidified (pH=5) with 10% HCl. Then, it is extracted with ethyl acetate. The organic phase is separated with 10% NaHCO$_3$ solution and washed with saturated NaCl solution, dried on MgSO$_4$, filtered, concentrated by evaporation and chromatographed on silica gel. 3-tert.-Butyldimethylsilyloxyestra-1,3,5(10)-17β-yl 4'-sulfamoylbenzoate is obtained.

Stage 2

3-Hydroxyestra-1,3,5(10)-17β-yl 4'-sulfamoylbenzoate (1)

500 mg of 3-tert.-butyldimethylsilyloxyestra-1,3,5(10)-17β-yl 4'-sulfamoylbenzoate is dissolved in 5 ml of THF, while being stirred, 500 mg of tetrabutylammonium fluoride (TBAF) is added at room temperature. After 1 hour, 20 ml of water is added. The substance is extracted with THF. The organic phase is washed with saturated NaCl solution, dried on MgSO$_4$, filtered, concentrated by evaporation and chromatographed on silica gel. 3-Hydroxyestra-1,3,5(10)-17β-yl 4'-sulfamoylbenzoate is obtained.

$^1$H-NMR (CDCl$_3$): 0.93 (s, 3H, H-18), 4.86 (m, 1H, H-17α), 7.56 (s, 2H, NH$_2$), 9.00 (s, 1H, OH)

EXAMPLE 2

3-Hydroxyestra-1,3,5(10)-trien-17β-yl 3'-sulfamoyl-4'-chloro-benzoate (3)

The substance is obtained analogously to Example 1 according to Variant 1 starting from 3-sulfamoyl-4-chloro-benzoic acid via the intermediate product 3-tert.-butyldimethylsilyloxyestra-1,3,5(10)-trien-17β-yl 3'-sulfamoyl-4'-chloro-benzoate (4).

$^1$H-NMR (DMSO-d$_6$): 0.92 (s, 3H, H-18), 4.87 (m, 1H, H-17), 7.82 (s, 2H, NH$_2$), 9.00 (s, 1H, 3-OH)

EXAMPLE 3

3-Hydroxyestra-1,3,5(10)-trien-17β-yl 2'-chloro-4'-fluoro-5'-sulfamoylbenzoate (5)

The substance is obtained analogously to Example 1 according to Variant 1 starting from 2-chloro-4-fluoro-5-sulfamoylbenzoic acid via the intermediate product 3-tert.-butyldimethylsilyloxyestra-1,3,5(10)-trien-17β-yl 2'-chloro-4'-fluoro-5'-sulfamoylbenzoate (6).

$^1$H-NMR (DMSO-d$_6$): 0.89 (s, 3H, H-18), 4.87 (m, 1H, H-17), 7.96 (s, 2H, NH$_2$), 9.02 (s, 1H, 3-OH)

EXAMPLE 4

3-Hydroxyestra-1,3,5(10)-trien-17β-yl 2',4'-dichloro-5'-sulfamoylbenzoate (7)

The substance is obtained analogously to Example 1 according to Variant 1 starting from 2,4-dichloro-5-sulfamoylbenzoic acid via the intermediate product 3-tert.-butyldimethylsilyloxyestra-1,3,5(10)-trien-17β-yl 2',4'-dichloro-5'-sulfamoylbenzoate (8).

$^1$H-NMR (DMSO-d$_6$): 0.88 (s, 3H, H-18), 4.87 (m, 1H, H-17), 7.86 (s, 2H, NH$_2$), 8.99 (s, 1H, 3-OH)

EXAMPLE 5

3-Hydroxyestra-1,3,5(10)-trien-17β-yl 3'-sulfamoylbenzoate (9)

Stage 1

3-tert.-Butyldimethylsilyloxyestra-1,3,5(10)-trien-17β-yl 3'-sulfamoylbenzoate (10)

1.0 g of 3-tert.-butyldimethylsilyloxyestra-1,3,5(10)-17β-ol is dissolved in 2 ml of pyridine and 2 ml of CHCl$_3$. 1.0 ml of 3-chlorosulfonylbenzoic acid chloride is added to the reaction mixture at −20° C. while being stirred. Then, it is heated to room temperature and stirred for 15 minutes. The reaction solution is added in 25 ml of concentrated NH$_3$ solution and stirred for 15 minutes. Then, the organic mobile solvent is distilled off. It is slightly acidified (pH=5) with 10% hydrochloric acid. The precipitated substance is suctioned off, washed with 10% NaHCO, solution and water and then dried. 3-tert.-Butyldimethylsilyl-oxyestra-1,3,5(10)-17β-yl 3'-sulfamoylbenzoate is obtained.

$^1$H-NMR (CDCl$_3$): 0.19 (s, 6H, Si-Me), 0.98 (s+s (superimposed), 12H, t.-C$_4$H$_9$, H-18), 4.96 (m, 1H, H-17), 5.08 (s, 2H, NH$_2$)

Stage 2

3-Hydroxyestra-1,3,5(10)-17β-yl 3'-sulfamoylbenzoate (9)

500 mg of 3-tert.-butyldimethylsilyloxyestra-1,3,5(10)-17β-yl 3'-sulfamoylbenzoate is dissolved in 10 ml of THF. 500 mg of TBAF is added at room temperature while being stirred. After 1 hour, 40 ml of water is stirred in, and then the organic mobile solvent is distilled off. The substance is filtered off, washed with water, dried and chromatographed on silica gel. 3-Hydroxyestra-1,3,5(10)-17β-yl 3'-sulfamoylbenzoate is obtained.

$^1$H-NMR (DMSO-d$_6$): 0.94 (s, 3H, H-18), 4.89 (m, 1H, H-17), 7.55 (s, 2H, NH$_2$) 9.00 (s, 1H, 3-OH)

EXAMPLE 6

3-Methoxyestra-1,3,5(10)-trien-17β-yl 3'-sulfamoylbenzoate (11)

1.0 g of 3-methoxyestra-1,3,5(10)-17β-ol is dissolved in 2 ml of pyridine and 2 ml of CHCl$_3$. 1.0 ml of 3-chlorosulfonylbenzoic acid chloride is added to the reaction mixture at −20° C. while being stirred. Then, it is heated to room temperature and stirred for 15 minutes. The reaction solution is added in 25 ml of concentrated NH$_3$ solution and stirred for another 15 minutes. Then, the organic mobile solvent is distilled off. It is slightly acidified (pH=5) with 10% hydrochloric acid. The precipitated substance is suctioned off, washed with 10% NaHCO$_3$ solution and water, dried, and chromatographed on silica gel. 3-Methoxyestra-1,3,5(10)-17β-yl 3'-sulfamoylbenzoate is obtained.

$^1$H-NMR (CDCl$_3$): 0.96 (s, 3H, H-18), 3.77 (s, 3H, OMe), 4.96 (m, 1H, H-17), 5.16 (s, 2H, NH$_2$)

EXAMPLE 7

3-Hydroxyestra-1,3,5(10)-trien-17β-yl 2'-methoxy-5'-sulfamoylbenzoate (12)

The substance is obtained analogously to Example 1 according to Variant 1 starting from 2-methoxy-5-sulfamoylbenzoic acid via the intermediate product 3-tert.-butyldimethylsilyloxyestra-1,3,5(10)-trien-17β-yl 2'-methoxy-5'-sulfamoylbenzoate (13).

$^1$H-NMR (DMSO-d$_6$): 0.88 (s, 3H, H-18), 3.91 (s, 3H, OMe), 4.82 (m, 1H, H-17), 7.36 (s, 2H, NH$_2$), 9.00 (s, 1H, 3-OH)

EXAMPLE 8

3-Benzoyloxyestra-1,3,5(10)-trien-17β-yl 3'-sulfamoylbenzoate (14)

1.0 g of 3-benzoyloxyestra-1,3,5(10)-17β-ol is dissolved in 2 ml of pyridine and 2 ml of CHCl$_3$. 1.0 ml of 3-chlorosulfonylbenzoic acid chloride is added to the reaction mixture at −20° C. while being stirred. Then, it is heated to room temperature and stirred for 15 minutes. The reaction solution is added in 30 ml of concentrated NH$_3$ solution and stirred for another 15 minutes. Then, the organic mobile solvent is distilled off. It is slightly acidified (pH=5) with 10% hydrochloric acid. The precipitated substance is suctioned off, washed with 10% NaHCO$_3$ solution and water, dried, and chromatographed on silica gel. 3-Methoxyestra-1,3,5(10)-17β-yl 3'-sulfamoylbenzoate is obtained.

$^1$H-NMR (CDCl$_3$): 0.97 (s, 3H, H-18), 4.91 (m, 1H, H-17), 7.56 (s, 2H, NH$_2$).

EXAMPLE 9

17β-(n-Pentanoyloxy)estra-1,3,5(10)-trien-3-yl 3'-sulfamoylbenzoate (15)

The substance is produced analogously to Example 9 starting from 3-hydroxyestra-1,3,5(10)-17β-yl valerate. 17β-(n-Pentanoyloxy)estra-1,3,5(10)-trien-3-yl 3'-sulfamoylbenzoate is obtained.

$^1$H-NMR (CDCl$_3$): 0.81 (s, 3H, H-18), 0.88 (t, 3H, CH$_3$), 4.64 (m, 1H, H-17), 7.58 (s, 2H, NH$_2$).

EXAMPLE 10

17β-Benzoyloxyestra-1,3,5(10)-trien-3-yl 3'-sulfamoylbenzoate (16)

The substance is produced analogously to Example 9 starting from 3-hydroxyestra-1,3,5(10)-17β-yl benzoate. 17β-Benzoyloxyestra-1,3,5(10)-trien-3-yl 3'-sulfamoylbenzoate is obtained.

$^1$H-NMR (CDCl$_3$): 0.96 (s, 3H, H-18), 4.86 (m, 1H, H-17), 7.59 (s, 2H, NH$_2$).

EXAMPLE 11

17β-Hydroxyestra-1,3,5(10)-trien-3-yl 4'-sulfamoylbenzoate (17)

The substance is obtained analogously to Example 1 according to Variant 1 starting from 4-sulfamoylbenzoic acid via the intermediate product 17β-tert.-butyldimethylsilyloxyestra-3,5(10)-trien-17β-yl 4'-sulfamoylbenzoate (18). After silylether cleavage, 17β-hydroxyestra-1,3,5(10)-trien-3-yl 4'-sulfamoylbenzoate (17) is obtained.

EXAMPLE 12

3-Hydroxyestra-1,3,5(10)-trien-17β-yl 2',3'-dimethoxy-5'-sulfamoylbenzoate (19)

The substance is obtained analogously to Example 1 according to Variant 1 starting from 2,3-dimethoxy-5-sulfamoylbenzoic acid via the intermediate product 3-tert.-butyldimethylsilyloxyestra-1,3,5(10)-trien-17β-yl 2',3'-dimethoxy-5'-sulfamoylbenzoate (20).

$^1$H-NMR (DMSO-d$_6$): 0.87 (s, 3H, H-18), 3.84 (s, 3H, OMe), 3.91 (s, 3H, OMe), 4.82 (m, 1H, H-17), 7.44 (s, 2H, NTH$^2$), 9.00 (s, 1H, 3-OH).

EXAMPLE 13

3-Hydroxyestra-1,3,5(10)-trien-17β-yl 2'-chloro-5'-sulfamoylbenzoate (21)

The substance is obtained analogously to Example 1 according to Variant 1 starting from 2-chloro-5-sulfamoylbenzoic acid via the intermediate product 3-tert.-butyldimethylsilyloxyestra-1,3,5(10)-trien-17β-yl 2'-chloro-5'-sulfamoylbenzoate (22).

$^1$H-NMR (DMSO-d$_6$): 0.89 (s, 3H, H-18), 4.89 (m, 1H, H-17), 7.63 (s, 2H, NH$_2$), 9.02 (s, 1H, 3-OH).

EXAMPLE 14

17β-Hydroxyestra-1,3,5(10)-trien-3-yl 2'-chloro-4'-fluoro-5'-sulfamoylbenzoate (23)

0.65 g of estradiol is dissolved in 7 ml of pyridine. After 0.8 g of 2-chloro-4-fluoro-5-sulfamoylbenzoic acid and 0.8 g of dicyclohexylcarbodiimide (DCC) are added, it is stirred for 3 hours at room temperature. Then, it is acidified with 10% HCl (pH=2). The precipitate is filtered off and washed with 10% NaHCO$_3$ solution and water. The product that is obtained is chromatographed on silica gel. 17β-Hydroxyestra-1,3,5(10)-3-yl 2'-chloro-4'-fluoro-5'-sulfamoylbenzoate (23) is obtained.

$^1$H-NMR (CD$_3$OD): 0.81 (s, 3H, H-18), 3.67(m, 1H, H-17).

$^{19}$F—NR (CD$_3$OD): −102.5 ppm.

EXAMPLE 15

17β-Hydroxyestra-1,3,5(10)-trien-3-yl 2',3'-dichloro-5'-sulfamoylbenzoate (24)

0.4 g of estradiol is dissolved in 7 ml of pyridine. After 0.8 g of 2,3-dichloro-5-sulfamoylbenzoic acid and 0.8 g of dicyclohexylcarbodiimide (DCC) are added, it is stirred for 1 hour at room temperature. Then, it is acidified with 10% HCl (pH=2), and 8 ml of water is added. The precipitate is filtered off and washed with 10% NaHCO$_3$ solution and water. The product that is obtained is chromatographed on silica gel. 17β-Hydroxyestra-1,3,5(10)-3-yl 2',3'-dichloro-5'-sulfamoylbenzoate (24) is obtained.

$^1$H-NMR (DMSO-d$_6$): 0.69 (s, 3H, H-18), 4.51 (m, 1H, H-17), 7.90 (s, 2H, NH$_2$).

EXAMPLE 16

3-Hydroxyestra-1,3,5(10)-trien-17β-yl 2'-sulfamoylbenzoate (25)

Stage 1

3-Benzoyloxyestra-1,3,5(10)-trien-17β-yl 2'-sulfobenzoate Ammonium Salt 10 g of estradiol-3-benzoate is dissolved in 100 ml of chloroform. After 5.0 g of 2-sulfobenzoic acid-cyclo-anhydride is added, it is stirred for 12 hours at 50° C. Then, it is cooled to 10° C. and mixed with a concentrated methanolic ammonia solution. The solvent is distilled off, and the residue is chromatographed on silica gel. 3-Benzoyloxyestra-1,3,5 (10)-trien-17β-yl 2'-sulfobenzoate ammonium salt is obtained.

$^1$H-NMR (DMSO-d$_6$): 0.82 (s, 3H, H-18), 4.78 (m, 1H, H-17), 7.35-8.10 (m (superimposed), 9H, benzoate).

Stage 2

3-Benzoyloxyestra-1,3,5(10)-trien-17β-yl 2'-chlorosulfonylbenzoate 3.0 g of 3-benzoyloxyestra-1,3,5(10)-trien-17β-yl 2'-sulfobenzoate ammonium salt is dissolved in 1 ml of DMF and 8 ml of SO$_2$Cl$_2$ under a cover gas. The reaction mixture is slightly refluxed for 4 hours. Then, it is cooled to 0° C., and the mixture is added to crushed ice. The cold mixture is extracted with ethyl acetate, and the organic phase is washed with 5% NaHCO$_3$ solution. After drying. on MgSO$_4$, it is filtered and concentrated by evaporation. 3-Benzoyloxyestra-1,3,5(10)-trien-17β-yl 2'-chlorosulfonylbenzoate, which can be used without further working-up, is obtained.

Stage 3

3-Benzoyloxyestra-1,3,5(10)-trien-17β-yl 2'-sulfamoylbenzoate (26)

2.0 g of 3-benzoyloxyestra-1,3,5(10)-trien-17β-yl 2'-chlorosulfonylbenzoate is dissolved in 10 ml of CHCl$_3$ and quickly stirred into 100 ml of 32% ammonia solution. After 10 hours of stirring at room temperature, the organic solvent is distilled off. The precipitated substance is suctioned off, washed several times with water, and dried. 3-Benzoyloxyestra-1,3,5(10)-trien-17β-yl 2'-sulfamoylbenzoate (26) is obtained at a higher purity.

$^1$H-NMR (DMSO-d$_6$): 0.86 (s, 3H, H-18), 4.87 (m, 1H, H-17), 7.33 (s, 2H, NH$_2$), 7.55-8.13 (m (superimposed), 9H, benzoate).

Stage 4

3-Hydroxyestra-1,3,5(10)-trien-17β-yl 2'-sulfamoylbenzoate (25)

530 mg of 3-benzoyloxyestra-1,3,5(10)-trien-17β-yl 2'-aminosulfonylbenzoate is dissolved in 90 ml of MeOH. 510 mg of Li$_2$CO$_3$ is added thereto. The reaction mixture is stirred for 12 hours at room temperature. After 10 ml of water is added, it is concentrated by evaporation. The precipitated substance is filtered off, washed with water, dried and chromatographed on silica gel. 3-Hydroxyestra-1,3,5(10)-trien-17β-yl 2'-sulfamoylbenzoate (25) is obtained.

$^1$H-NMR (DMSO-d$_6$): 0.83 (s, 3H, H-18), 4.84 (m, 1H, H-17), 7.25 (s, 2H, NH$_2$), 7.60-8.00 (m, 4H, benzoate), 9.00 (s, 1H, 3-OH).

EXAMPLE 17

Estra-1,3,5(10)-trien-3,17β-diyl bis(3'-sulfamoylbenzoate) (27)

1.0 g of estradiol is dissolved in 4 ml of pyridine. 2.0 ml of 3-chlorosulfonylbenzoic acid chloride is added to the reaction mixture at −20° C. while being stirred. Then, it is heated to room temperature and stirred for 15 minutes. The reaction solution is added in 50 ml of concentrated NH$_3$ solution and stirred for 15 minutes. Then, the organic solvent is distilled off. It is acidified with 10% hydrochloric acid (pH=3). The precipitated substance is suctioned off, washed with 10% NaHCO$_3$ solution and water, and then dried. Estra-1,3,5(10)-triene-3,17β-diyl bis(3'-sulfamoylbenzoate) (27) is obtained.

$^1$H-NMR (DMSO-d$_6$): 0.98 (s, 3H, H-18), 4.91 (m, 1H, H-17), 9.98-7.43 (m, 3H, H—Ar (steroid)), 7.65-8.58 (m(superimposed), 8H, H—Ar)).

EXAMPLE 18

3-tert.-Butyldimethylsilyloxyestra-1,3,5(10)-trien-17β-yl 2'-chloro-4'-sulfamoylbenzoate (28)

1.0 g of 3-tert.-butyldimethylsilyloxyestra-1,3,5(10)-17β-ol is dissolved in 20 ml of pyridine. After 1.5 g of 2-chloro-4-sulfamoylbenzoic acid, 250 mg of p-toluenesulfonic acid and 1.5 g of DCC are added, it is stirred for 48 hours at room temperature. Then, 100 ml of water and 30 ml of CHCl$_3$ are added. It is slightly acidified (pH=5) with 10% HCl. The precipitate is filtered off and rewashed with CHCl$_3$. The organic phase is separated with 10% NaHCO$_3$ solution and saturated NaCl solution, dried on MgSO$_4$, filtered, concentrated by evaporation and chromatographed on silica gel. 3-tert.-Butyldimethylsilyloxyestra-1,3,5(10)-17β-yl 2'-chloro-4'-sulfamoylbenzoate is obtained.

$^1$H-NMR (DMSO-d$_6$): 0.16 (s, 6H, Si-Me), 0.88 (s, 3H, H-18), 0.94 (s, 9H, t.-C$_4$H$_9$) 4.89 (t, 1H, H-17), 7.66 (s, 2H, NH$_2$)

EXAMPLE 19

3-Hydroxyestra-1,3,5(10)-trien-17β-yl 2'-chloro-4'-sulfamoylbenzoate (29)

300 mg of 3-tert.-butyldimethylsilyloxyestra-1,3,5(10)-17β-yl 2'-chloro-4'-sulfamoylbenzoate is dissolved in 25 ml of THF. 180 mg of TBAF is added at room temperature while being stirred. After 1 hour, 20 ml of water is stirred in. The substance is extracted with ethyl acetate. The organic phase is washed with saturated NaCl solution, dried on MgSO$_4$, filtered, concentrated by evaporation and chromatographed on silica gel. 3-Hydroxyestra-1,3,5(10)-17β-yl 2'-chloro-4'-sulfamoylbenzoate is obtained.

$^1$H-NMR (DMSO-d$_6$): 0.87 (s, 3H, H-18), 4.88 (t, 1H, H-17), 7.66 (s, 2H, NH$_2$), 9.00 (s, 1H, 3-OH)

LITERATURE (1) Cummings, S. R.; Browner, W. S.; Bauer, D.; Stone, K.; Ensrud, K.; Jamal, S. and Ettinger, B. (1998), Endogenous Hormones and the Risk of Hip and Vertebral Fractures Among Older Women. N. Engl. J. Med. 339, 733-38/ Gustafsson, J. A. (2000), Novel Aspects of Estrogen Action. J. Soc. Gynecol. Investig. 7, p. 8-p. 9.

(2) Frank, G. R. (1995), The Role of Estrogen in Pubertal Skeletal Physiology: Epiphyseal Maturation and Mineralization of the Skeleton. Acta Paediatr. 84(6), 627-30.

(3) Mashchak, C. A.; Lobo, R. A.; Dozono-Takano, R.; Eggena, P.; Nakamura, R. M.; Brenner, P. F. and Mishell, D. R., Jr. (1982), Comparison of Pharmacodynamic Properties of Various Estrogen Formulations. Am. J. Obstet. Gynecol. 144, 511-18.

(4) Goldzieher, J. W. (1990), Selected Aspects of the Pharmacokinetics and Metabolism of Ethinyl Estrogens and their Clinical Implications. Am. J. Obstet. Gynecol. 163, 318-22, Mandel, F. P.; Geola, F. L.; Lu, J. K. H.; Eggena, P.; Sambhi, M. P.; Hershlnan, J. M. and Judd, H. L. (1982), Biologic Effects of Various Doses of Ethinyl Estradiol in Postmenopausal Women. Obstet. Gynecol. 59, 673-9/ Mashchak, C. A.; Lobo, R. A.; Dozono-Takano, R.; Eggena, P.; Nakamura, R. M:; Brenner, P. F. and Mishell, D. R., Jr. (1982), Comparison of Pharmacodynamic Properties of Various Estrogen Formulations. Am. J. Obstet. Gynecol. 144, 511-18.

(5) Helmer, O. M. and Griffith, R. S. (1952), The Effect of the Administration of Estrogens on the Renin-Substrate (Hypertensinogen) Content on Rat Plasma. Endocrinology 51, 421-6/Krattenmacher, R.; Knauthe, R.; Parczyk, K.; Walker, A.; Hilgenfeldt, U. and Fritzemeier, K.-H. (1994), Estrogen Action on Hepatic Synthesis of Angiotensinogen and IGF-I: Direct and Indirect Estrogen Effects. J. Steroid. Biochem. Mol. Biol. 48, 207-14/Oelkers, W. K. H. (1996), Effects of Estrogens and Progestagens on the Renin-Aldosterone System and Blood Pressure. Steroids 61, 166-71/O'Sullivan, A. J. and Ho, K. K. Y. (1995), A Comparison of the Effects of Oral and Transdermal Estrogen Replacement on Insulin Sensitivity in Postmenopausal Women. J. Clin. Endocrinol. Metab. 80, 1783-8/by Schoultz, B.; Carlström, K.; Collste, L.; Eriksson, A.; Henriksson, P.; Pousette, A. and Stege, R. (1989), Estrogen Therapy and Liver Function—Metabolic Effects of Oral and Parenteral Administration. Prostate 14, 389-95.

(6) Le Roith and Butler, A. A. (1999), Insulin-like Growth Factors in Pediatric Health and Disease. J. Clin. Endocrinol. Metab. 84, 4355-61.

(7) O'Sullivan, A. J. and Ho, K. K. Y. (1995), A Comparison of the Effects of Oral and Transdermal Estrogen Replacement on Insulin Sensitivity in Postmenopausal Women. J. Clin. Endocrinol. Metab. 80, 1783-8/Span, J. P. T.; Pieters, G. F. F. M.; Sweep, C. G. J.; Hermus, A. R. M. M. and Smals, A. G. H. (2000), Gender Difference in Insulin-like Growth Factor I Response to Growth Hormone (GH) Treatment in GH-Deficient Adults: Role of Sex Hormone Replacement. J. Clin. Endocrinol. Metab. 85, 1121-5/ Kelly, J. J.; Rajkovic, I. A.; O'Sullivan, A. J.; Sernia, C. and Ho, K. K. Y. (1993), Effects of Different Oral Estrogen Formulations on Insulin-like Growth Factor-I, Growth Hormone and Growth Hormone-Binding Protein in Post-Menopausal Women. Clin. Endocrinol. 39, 561-67.

(8) C. Landolfi; M. Marchetti; G. Ciocci; and C. Milanese, Journal of Pharmacological and Toxicological Methods 38, 169-172 (1997).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102004025966.6, filed May 21, 2004, and U.S. Provisional Application Ser. No. 60/572,964, filed May 21, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various. usages and conditions.

Figure 1:
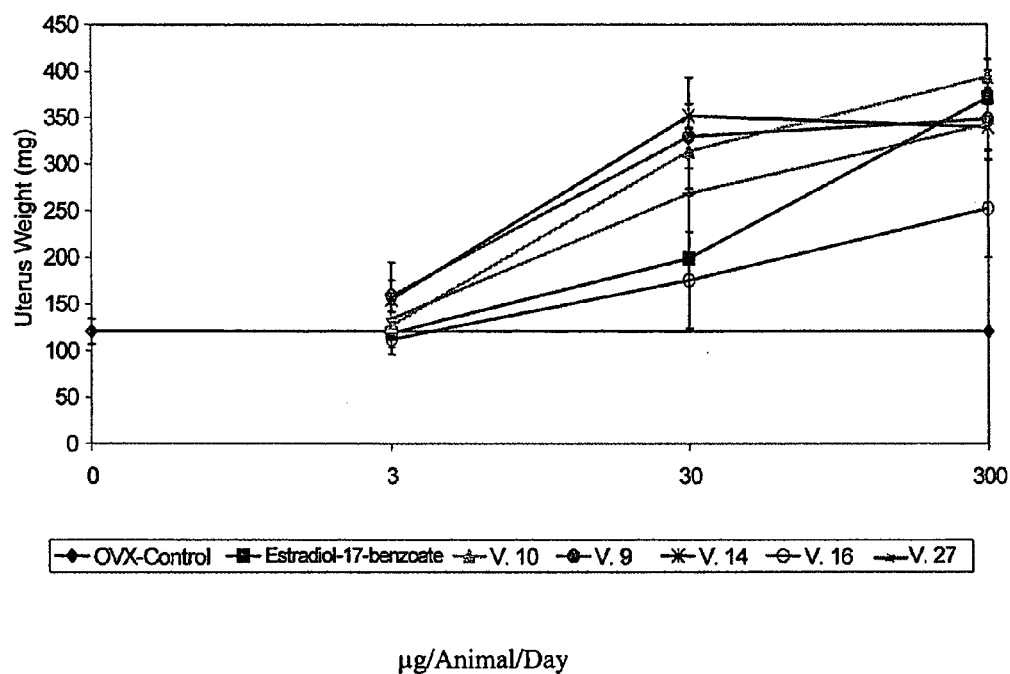
FIG. 1: depicts the induction of uterus growth in ovariectomized rats.
Figure 2:
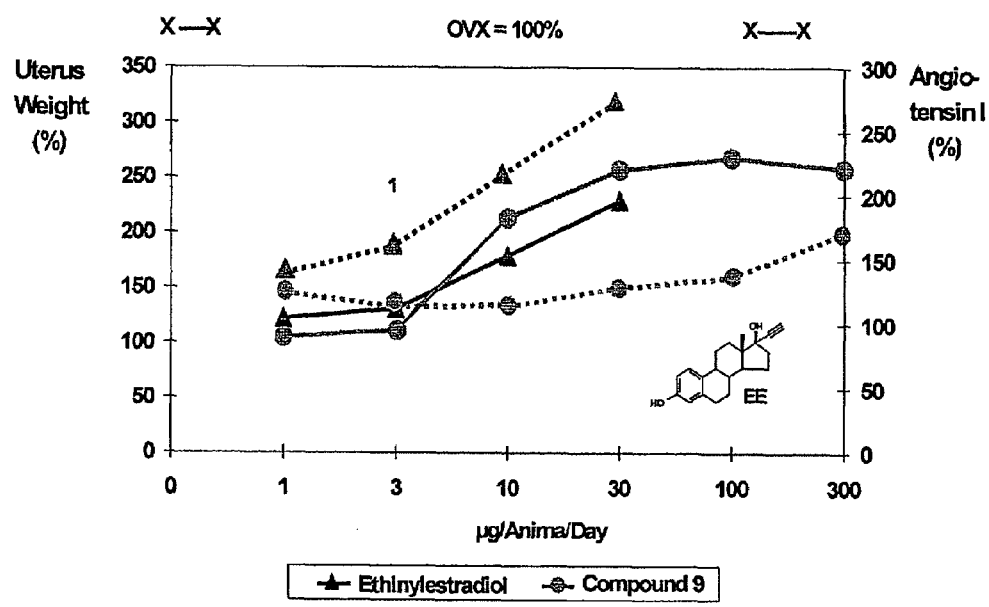
FIG. 2: depicts estrogenic activity and liver estrogeneity of compound 1.

The invention claimed is:

1. An estradiol compound of formula (I)

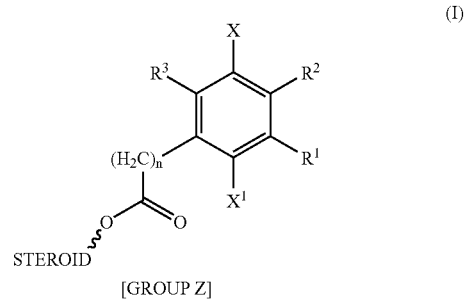

in which n is a number 0-4,
R$^1$ is a radical —SO$_2$NH$_2$ or —NHSO$_2$NH$_2$,
  wherein
  R$^2$, R$^3$, X, and X$^1$ stand for a hydrogen atom, a halogen atom,
    a nitrile group, a nitro group, a branched or straight chain, substituted or unsubstituted C$_{1-5}$-alkyl group, a C$_p$F$_{2p+1}$ group with p=1-3, a group OC(O)—R$^{20}$, COOR$^{20}$, OR$^{20}$, C(O)NHR$^{20}$ or OC(O)NH—R$^{21}$,
  wherein
    R$^{20}$, and R$^{21}$ are a branched or straight chain, substituted or unsubstituted C$_{1-5}$-alkyl group, a mono or bicyclic C$_{3-8}$-cycloalkyl group, a substituted or unsubstituted C$_6$ to C$_{15}$ aryl group, a substituted or unsubstituted C$_{1-4}$-alkylene aryl group, a substituted or unsubstituted C$_{1-4}$-alkylene-C$_{3-8}$-cycloalkyl group or a substituted or unsubstituted C$_{3-8}$-cycloalkylene-C$_{1-4}$-alkyl group, and
    R$^{20}$ in addition is hydrogen, or $R^2$ is a radical —SO$_2$NH$_2$ or —NHSO$_2$NH$_2$,
wherein
$R^1$, $R^3$, X, and $X^1$ stand for a hydrogen atom, a halogen atom,
a nitrile group, a nitro group, a branched or straight chain, substituted or unsubstituted C$_{1-5}$-alkyl group, a C$_p$F$_{2p+1}$ group with p=1-3, a group OC(O)—R$^{20}$, COOR$^{20}$, OR$^{20}$, C(O)NHR$^{20}$ or OC(O)NH—R$^{21}$,
wherein
$R^{20}$, and $R^{21}$ are a branched or straight chain, substituted or unsubstituted C$_{1-5}$-alkyl group, a mono or bicyclic C$_{3-8}$-cycloalkyl group, a substituted or unsubstituted C$_6$ to C$_{15}$ aryl group, a substituted or unsubstituted C$_{1-4}$-alkylene aryl group, a substituted or unsubstituted C$_{1-4}$-alkylene-C$_{3-8}$-cycloalkyl group or a substituted or unsubstituted C$_{3-8}$-cycloalkylene-C$_{1-4}$-alkyl group, and
$R^{20}$ in addition is hydrogen, or
$R^3$ is a radical —SO$_2$NH$_2$ or —NHSO$_2$NH$_2$,
wherein
$R^1$, $R^2$, X, and $X^1$ stand for a hydrogen atom, a halogen atom,
a nitrile group, a nitro group, a branched or straight chain, substituted or unsubstituted C$_{1-5}$-alkyl group, a C$_p$F$_{2p+1}$ group with p=1-3, a group OC(O)—R$^{20}$, COOR$^{20}$, OR$^{20}$, C(O)NHR$^{20}$ or OC(O)NH—R$^{21}$,
wherein
$R^{20}$, and $R^{21}$ are a branched or straight chain, substituted or unsubstituted C$_{1-5}$-alkyl group, a mono or bicyclic C$_{3-8}$-cycloalkyl group, a substituted or unsubstituted C$_6$ to C$_{15}$ aryl group, a substituted or unsubstituted C$_{1-4}$-alkylene aryl group, a substituted or unsubstituted C$_{1-4}$-alkylene-C$_{3-8}$-cycloalkyl group or a substituted or unsubstituted C$_{3-8}$-cycloalkylene-C$_{1-4}$-alkyl group, and
$R^{20}$ in addition is hydrogen, and
STEROID stands for a steroidal ABCD-ring system of formula (II A) or (II B),

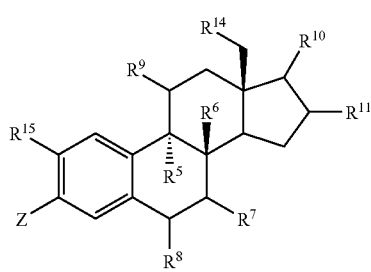

II A

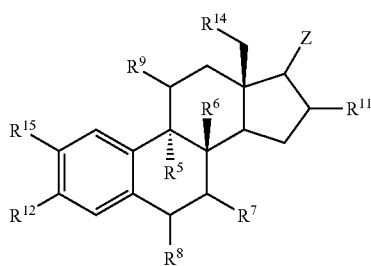

II B wherein
Z is group Z, $R^5$, $R^6$ and $R^8$ in each case represent a hydrogen atom, and
$R^7$ represents a hydrogen atom, a methyl group or an ethyl group, or
$R^5$+$R^6$, $R^7$+$R^8$ or $R^6$+$R^7$ together represent a double bond,
$R^9$ represents a hydrogen atom, a halogen atom, a hydroxy group, a methoxy group, a group OC(O)—R$^{20}$, a methyl or ethyl group,
$R^{10}$ represents a hydroxy group, a methoxy group, a tri (C$_{1-6}$-alkyl)silyloxy group, a group OC(O)—R$^{20}$, a C$_{2-5}$-heterocycloalkyloxy group or a group Z,
$R^{11}$ represents a hydrogen atom or a halogen atom,
$R^{12}$ represents a hydroxy group, a methoxy group, a tri(C$_1$-C$_6$-alkyl)silyloxy group, a group OC(O)—R$^{20}$, a C$_{2-5}$-heterocycloalkyloxy group or a group Z,
$R^{14}$ represents a hydrogen atom, a methyl group, or an ethyl group,
$R^{15}$ represents a hydrogen atom, a hydroxy group, a methoxy group, an ethoxy group, a tri(C$_{1-6}$-alkyl)silyloxy group, a group OC(O)—R$^{20}$ or a C$_{25}$-heterocycloalkyloxy group,
or a pharmaceutically acceptable salt thereof.

2. A compound according to claim 1, wherein n is 0, 1 or 2.
3. A compound according to claim 1, wherein $R^1$ represents a radical —SO$_2$NH$_2$ or —NHSO$_2$NH$_2$.
4. A compound according to claim 3, wherein $R^1$ represents a group —SO$_2$NH$_2$.
5. A compound according to claim 1, wherein either $R^1$, $R^2$ or $R^3$ a group —SO$_2$NH$_2$.
6. A compound according to claim 1, wherein
if $R^1$ means —SO$_2$NH$_2$ or —NHSO$_2$NH$_2$, then $R^2$, $R^3$, X, and $X^1$, independently of one another, stand for a hydrogen atom, a fluorine atom, a chlorine atom, a hydroxy group or a methoxy group, or
if $R^2$ means —SO$_2$NH$_2$ or —NHSO$_2$NH$_2$, then $R^1$, $R^3$, X, and $X^1$, independently of one another, stand for a hydrogen atom, a fluorine atom, a chlorine atom, a hydroxy group or a methoxy group, or
if $R^3$ means —SO$_2$NH$_2$ or —NHSO$_2$NH$_2$, then $R^1$, $R^2$, X, and $X^1$, independently of one another, stand for a hydrogen atom, a fluorine atom, a chlorine atom, a hydroxy group or a methoxy group.

7. A compound according to claim 1, wherein, independently of one another,
$R^5$, $R^6$, $R^7$ and $R^8$ in each case represent a hydrogen atom,
$R^9$ represents a hydrogen atom or a fluorine atom,
$R^{11}$ represents a hydrogen atom or a fluorine atom,
$R^{10}$ represents a hydroxy group, a methoxy group, a trimethylsilyloxy radical, a tert.-butyldimethylsilyloxy radical, a benzoate radical, an acetate radical, a propionate radical, a valerate radical, a (trans-4-n-butyl) cyclohexylcarboxylate radical, a cyclopentylpropionate radical or a group Z,
$R^{12}$ represents a hydroxy group, a methoxy group, a trimethylsilyloxy radical, a tert.-butyldimethylsilyloxy radical, a benzoate radical, an acetate radical, a propionate radical, a valerate radical, a (trans-4-n-butyl) cyclohexylcarboxylate radical, a cyclopentylpropionate radical or a group Z,
$R^{14}$ represents a hydrogen atom, and
$R^{15}$ represents a hydrogen atom, a methoxy group, or an ethoxy group.

8. A compound according to claim 1, wherein n is 0.
9. A compound according to claim 1, wherein n is 2.
10. A compound according to claim 1, wherein n is 3.
11. A compound according to claim 1, wherein n is 4.
12. A compound according to claim 7, wherein, independently of one another, $R^{10}$ represents a hydroxy group, a methoxy group, a trimethylsilyloxy radical, a tert.-butyldimethylsilyloxy radical, a benzoate radical, an acetate radical, a propionate radical, a valerate radical, a cyclopentylpropionate radical or a group Z, and $R^{12}$ represents a hydroxy group, a methoxy group, a trimethylsilyloxy radical, a tert.-butyldimethylsilyloxy radical, a benzoate radical, an acetate radical, a propionate radical, a valerate radical, a cyclopentylpropionate radical or a group Z.

13. A compound according to claim 1, wherein $R^1$ is a radical —$SO_2NH_2$ or —$NHSO_2NH_2$, wherein $R^2$, $R^3$, X, and $X^1$ stand for a hydrogen atom, a halogen atom, a nitrile group, a nitro group, a branched or straight chain, unsubstituted $C_{1-5}$-alkyl group, a $C_pF_{2p+1}$ group with p=1-3, a group OC(O)—$R^{20}$, COOR$^{20}$, OR$^{20}$, C(O)NHR$^{20}$ or OC(O)NH—$R^{21}$, wherein $R^{20}$, and $R^{21}$ are a branched or straight chain, unsubstituted $C_{1-5}$-alkyl group, a mono or bicyclic $C_{3-8}$-cycloalkyl group, an unsubstituted $C_6$ to $C_{15}$ aryl group, an unsubstituted $C_{1-4}$-alkylene aryl group, an unsubstituted $C_{1-4}$-alkylene-$C_{3-8}$-cycloalkyl group or an unsubstituted $C_{3-8}$-cycloalkylene-$C_{1-4}$-alkyl group, and $R^{20}$ R in addition can mean a hydrogen, or $R^2$ is a radical —$SO_2NH_2$ or —$NHSO_2NH_2$, wherein $R^1$, $R^3$, X, and $X^1$ stand for a hydrogen atom, a halogen atom, a nitrile group, a nitro group, a branched or straight chain, unsubstituted $C_{1-5}$-alkyl group, a $C_pF_{2p+1}$ group with p=1-3, a group OC(O)—$R^{20}$, COOR$^{20}$, OR$^{20}$, C(O)NHR$^{20}$ or OC(O)NH—$R^{21}$, wherein $R^{20}$, and $R^{21}$ are a branched or straight chain, unsubstituted $C_{1-5}$-alkyl group, a mono or bicyclic $C_{3-8}$-cycloalkyl group, an unsubstituted $C_6$ to $C_{15}$ aryl group, an unsubstituted $C_{1-4}$-alkylene aryl group, an unsubstituted $C_{1-4}$-alkylene-$C_{3-8}$-cycloalkyl group or an unsubstituted $C_{3-8}$-cycloalkylene-$C_{1-4}$-alkyl group, and $R^{20}$ in addition can mean a hydrogen, or $R^3$ is a radical —$SO_2NH_2$ or —$NHSO_2NH_2$, wherein $R^1$, $R^2$, X, and $X^1$ stand for a hydrogen atom, a halogen atom, a nitrile group, a nitro group, a branched or straight chain, unsubstituted $C_{1-5}$-alkyl group, a $C_pF_{2p+1}$ group with p=1-3, a group OC(O)—$R^{20}$, COOR$^{20}$, OR$^{20}$, C(O)NHR$^{20}$ or OC(O)NH—$R^{21}$, wherein $R^{20}$, and $R^{21}$ are a branched or straight chain, unsubstituted $C_{1-5}$-alkyl group, a mono or bicyclic $C_{3-8}$-cycloalkyl group, an unsubstituted $C_6$ to $C_{15}$ aryl group, an unsubstituted $C_{1-4}$-alkylene aryl group, an unsubstituted $C_{1-4}$-alkylene-$C_{3-8}$-cycloalkyl group or an unsubstituted $C_{3-8}$-cycloalkylene-$C_{1-4}$-alkyl group, and $R^{20}$ addition can mean a hydrogen.

14. A compound according to claim 1, wherein $R^1$ is a radical —$SO_2NH_2$ or —$NHSO_2NH_2$, wherein $R^2$, $R^3$, X, and $X^1$ stand for a hydrogen atom, a halogen atom, a nitrile group, a nitro group, a branched or straight chain, substituted or unsubstituted $C_{1-5}$-alkyl group, wherein the substituent on the $C_{1-5}$-alkyl group is a halogen atom, a hydroxy group, or a nitrile group, a $C_pF_{2p+1}$ group with p=1-3, a group OC(O)—$R^{20}$, COOR$^{20}$, OR$^{20}$, C(O)NHR$^{20}$ or OC(O)NH—$R^{21}$, wherein $R^{20}$, and $R^{21}$ are a branched or straight chain, substituted or unsubstituted $C_{1-5}$-alkyl group, wherein the substituent on the $C_{1-5}$-alkyl group is a halogen atom, a hydroxy group, or a nitrile group, a mono or bicyclic $C_{3-8}$-cycloalkyl group, a substituted or unsubstituted $C_6$ to $C_{15}$ aryl group, wherein the substituent on the aryl group is a halogen atom or a nitro group, a substituted or unsubstituted $C_{1-4}$-alkylene aryl group, wherein the substituent on the $C_{1-4}$-alkylene aryl group is a halogen atom, a substituted or unsubstituted $C_{1-4}$-alkylene-$C_{3-8}$-cycloalkyl group, wherein the substituent on the $C_{1-4}$-alkylene-$C_{3-8}$-cycloalkyl group is a halogen atom, or a substituted or unsubstituted $C_{3-8}$-cycloalkylene-$C_{1-4}$-alkyl group, wherein the substituent on the $C_{3-8}$-cycloalkylene-$C_{1-4}$-alkyl group is a halogen atom, and $R^{20}$ in addition is hydrogen, or $R^2$ is a radical —$SO_2NH_2$ or —$NHSO_2NH_2$, wherein $R^1$, $R^3$, X, and $X^1$ stand for a hydrogen atom, a halogen atom, a nitrile group, a nitro group, a branched or straight chain, substituted or unsubstituted $C_{1-5}$-alkyl group, wherein the substituent on the $C_{1-5}$-alkyl group is a halogen atom, a hydroxy group, or a nitrile group, a $C_pF_{2p+1}$ group with p=1-3, a group OC(O)—$R^{20}$, COOR$^{20}$, OR$^{20}$, C(O)NHR$^{20}$ or OC(O)NH—$R^{21}$, wherein $R^{20}$, and $R^{21}$ are a branched or straight chain, substituted or unsubstituted $C_{1-5}$-alkyl group, wherein the substituent on the $C_{1-5}$-alkyl group is a halogen atom, a hydroxy group, or a nitrile group, a mono or bicyclic $C_{3-8}$-cycloalkyl group, a substituted or unsubstituted $C_6$ to $C_{15}$ aryl group, wherein the substituent on the aryl group is a halogen atom or a nitro group, a substituted or unsubstituted $C_{1-4}$-alkylene aryl group, wherein the substituent on the $C_{1-4}$-alkylene aryl group is a halogen atom, a substituted or unsubstituted $C_{1-4}$-alkylene-$C_{3-8}$-cycloalkyl group, wherein the substituent on the $C_{1-4}$-alkylene-$C_{3-8}$-cycloalkyl group is a halogen atom, or a substituted or unsubstituted $C_{3-8}$-cycloalkylene-$C_{1-4}$-alkyl group, wherein the substituent on the $C_{3-8}$-cycloalkylene-$C_{1-4}$-alkyl group is a halogen atom, and $R^{20}$ in addition is hydrogen, or $R^3$ is a radical —$SO_2NH_2$ or —$NHSO_2NH_2$,
wherein
$R^1$, $R^2$, X, and $X^1$ stand for a hydrogen atom, a halogen atom,
a nitrile group, a nitro group,
a branched or straight chain, substituted or unsubstituted $C_{1-5}$-alkyl group,
wherein the substituent on the $C_{1-5}$-alkyl group is a halogen atom, a hydroxy group, or a nitrile group,
a $C_pF_{2p+1}$ group with p=1-3, a group OC(O)—$R^{20}$, COO$R^{20}$, O$R^{20}$, C(O)NH$R^{20}$ or OC(O)NH—$R^{21}$,
wherein
$R^{20}$, and $R^{21}$ are
a branched or straight chain, substituted or unsubstituted $C_{1-5}$-alkyl group,
wherein the substituent on the $C_{1-5}$-alkyl group is a halogen atom, a hydroxy group, or a nitrile group,
a mono or bicyclic $C_{3-8}$-cycloalkyl group,
a substituted or unsubstituted $C_6$ to $C_{15}$ aryl group, wherein the substituent on the aryl group is a halogen atom or a nitro group,
a substituted or unsubstituted $C_{1-4}$-alkylene aryl group, wherein the substituent on the $C_{1-4}$-alkylene aryl group is a halogen atom,
a substituted or unsubstituted $C_{1-4}$-alkylene-$C_{3-8}$-cycloalkyl group, wherein the substituent on the $C_{1-4}$-alkylene-$C_{3-8}$-cycloalkyl group is a halogen atom, or
a substituted or unsubstituted $C_{3-8}$-cycloalkylene-$C_{1-4}$-alkyl group, wherein the substituent on the $C_{3-8}$-cycloalkylene-$C_{1-4}$-alkyl group is a halogen atom,
and
$R^{20}$ in addition is hydrogen.

15. A compound according to claim 1, which is
3-Hydroxyestra-1,3,5(10)-trien-17β-yl 3'-sulfamoylbenzoate,
3-Acetoxyestra-1,3,5(10)-trien-17β-yl 3'-sulfamoylbenzoate,
3-tert.-Butyldimethylsilyloxyestra-1,3,5(10)-trien-17β-yl 3'-sulfamoylbenzoate,
3-Hydroxyestra-1,3,5(10)-trien-17β-yl 2'-chloro-5'-sulfamoylbenzoate,
3-Hydroxyestra-1,3,5(10)-trien-17β-yl 3'-sulfamoyl-4'-chloro-benzoate,
3-Hydroxyestra-1,3,5(10)-trien-17β-yl 2',4'-dichloro-5'-sulfamoylbenzoate,
3-Hydroxyestra-1,3,5(10)-trien-17β-yl 2'-chloro-4'-fluoro-5'-sulfamoylbenzoate,
3-Hydroxyestra-1,3,5(10)-trien-17β-yl 2'-methoxy-5'-sulfamoylbenzoate,
3-tert.-Butyldimethylsilyloxyestra-1,3,5(10)-trien-17β-yl 2'-methoxy-5'-sulfamoylbenzoate
3-Hydroxyestra-1,3,5(10)-trien-17β-yl 2',3'-dimethoxy-5'-sulfamoylbenzoate,
3-Hydroxyestra-1,3,5(10)-trien-17β-yl 4'-sulfamoylbenzoate,
2-Methoxy-3-hydroxyestra-1,3,5(10)-trien-17β-yl 3'-sulfamoylbenzoate,
2-Methoxy-3-hydroxyestra-1,3,5(10)-trien-17β-yl 2'-chloro-5'-sulfamoylbenzoate,
2-Methoxy-3-hydroxyestra-1,3,5(10)-trien-17β-yl 3'-sulfamoyl-4'-chloro-benzoate,
2-Methoxy-3-hydroxyestra-1,3,5(10)-trien-17β-yl 2',4'-dichloro-5'-sulfamoyl-benzoate,
2-Methoxy-3-hydroxyestra-1,3,5(10)-trien-17β-yl 2'-chloro-4'-fluoro-5'-sulfamoylbenzoate,
2-Methoxy-3-hydroxyestra-1,3,5(10)-trien-17β-yl 4'-sulfamoylbenzoate,
2-Methoxy-3-hydroxyestra-1,3,5(10)-trien-17β-yl 4'-sulfamatobenzoate,
3-Benzoyloxyestra-1,3,5(10)-trien-17β-yl 3'-sulfamoylbenzoate,
17β-(n-Pentanoyloxy)estra-1,3,5(10)-trien-3-yl 3'-sulfamoylbenzoate,
17β-Benzoyloxyestra-1,3,5(10)-trien-3-yl 3'-sulfamoylbenzoate,
17β-Hydroxyestra-1,3,5(10)-trien-3-yl 4'-sulfamoylbenzoate,
17β-Hydroxyestra-1,3,5(10)-trien-3-yl 2',3'-dichloro-5'-sulfamoylbenzoate,
17β-Hydroxyestra-1,3,5(10)-trien-3-yl 2'-chloro-4'-fluoro-5'-sulfamoylbenzoate,
3-Methoxyestra-1,3,5(10)-trien-17β-yl 3'-sulfamoylbenzoate,
3-Hydroxyestra-1,3,5(10)-trien-17β-yl 2'-sulfamoylbenzoate,
3-Benzoyloxyestra-1,3,5(10)-trien-17β-yl 2'-sulfamoylbenzoate,
2-Methoxy-3-hydroxyestra-1,3,5(10)-trien-17β-yl 2',3'-dimethoxy-5'-sulfamoylbenzoate,
Estra-1,3,5(10)-triene-3,17β-diyl bis(3'-sulfamoylbenzoate),
2-Ethoxy-3-hydroxyestra-1,3,5(10)-trien-17β-yl 3'-sulfamoylbenzoate,
2-Ethoxy-3-hydroxyestra-1,3,5(10)-trien-17β-yl 2'-chloro-5'-sulfamoylbenzoate,
2-Ethoxy-3-hydroxyestra-1,3,5(10)-trien-17β-yl 3'-sulfamoyl-4'-chloro-benzoate,
2-Ethoxy-3-hydroxyestra-1,3,5(10)-trien-17β-yl 2',4'-dichloro-5'-sulfamoyl-benzoate,
2-Ethoxy-3-hydroxyestra-1,3,5(10)-trien-17β-yl 2'-chloro-4'-fluoro-5'-sulfamoylbenzoate,
2-Ethoxy-3-hydroxyestra-1,3,5(10)-trien-17β-yl 4'-sulfamoylbenzoate,
2-Ethoxy-3-hydroxyestra-1,3,5(10)-trien-17β-yl 4'-sulfamatobenzoate,
2-Ethoxy-3-hydroxyestra-1,3,5(10)-trien-17β-yl 2',3'-dimethoxy-5'-sulfamoylbenzoate,
3-tert.-Butyldimethylsilyloxyestra-1,3,5(10)-trien-17β-yl 2'-chloro-4'-sulfamoylbenzoate, or
3-Hydroxyestra-1,3,5(10)-trien-17β-yl 2'-chloro-4'-sulfamoylbenzoate.

16. A compound according to claim 1, which is
3-Hydroxyestra-1,3,5(10)-trien-17β-yl 3'-sulfamoylbenzoate,
3-Acetoxyestra-1,3,5(10)-trien-17β-yl 3'-sulfamoylbenzoate,
3-tert.-Butyldimethylsilyloxyestra-1,3,5(10)-trien-17β-yl 3'-sulfamoylbenzoate,
3-Hydroxyestra-1,3,5(10)-trien-17β-yl 2'-chloro-5'-sulfamoylbenzoate,
3-Hydroxyestra-1,3,5(10)-trien-17β-yl 3'-sulfamoyl-4'-chloro-benzoate,
3-Hydroxyestra-1,3,5(10)-trien-17β-yl 2',4'-dichloro-5'-sulfamoylbenzoate,
3-Hydroxyestra-1,3,5(10)-trien-17β-yl 2'-chloro-4'-fluoro-5'-sulfamoylbenzoate,
3-Hydroxyestra-1,3,5(10)-trien-17β-yl 2'-methoxy-5'-sulfamoylbenzoate,
3-tert.-Butyldimethylsilyloxyestra-1,3,5(10)-trien-17β-yl 2'-methoxy-5'-sulfamoylbenzoate
3-Hydroxyestra-1,3,5(10)-trien-17β-yl 2',3'-dimethoxy-5'-sulfamoylbenzoate,
3-Hydroxyestra-1,3,5(10)-trien-17β-yl 4'-sulfamoylbenzoate, 2-Methoxy-3-hydroxyestra-1,3,5(10)-trien-17β-yl 3'-sulfamoylbenzoate,
2-Methoxy-3-hydroxyestra-1,3,5(10)-trien-17β-yl 2'-chloro-5'-sulfamoylbenzoate,
2-Methoxy-3-hydroxyestra-1,3,5(10)-trien-17β-yl 3'-sulfamoyl-4'-chloro-benzoate,
2-Methoxy-3-hydroxyestra-1,3,5(10)-trien-17β-yl 2',4'-dichloro-5'-sulfamoyl-benzoate,
2-Methoxy-3-hydroxyestra-1,3,5(10)-trien-17β-yl 2'-chloro-4'-fluoro-5'-sulfamoylbenzoate,
2-Methoxy-3-hydroxyestra-1,3,5(10)-trien-17β-yl 4'-sulfamoylbenzoate,
2-Methoxy-3-hydroxyestra-1,3,5(10)-trien-17β-yl 4'-sulfamatobenzoate,
3-Benzoyloxyestra-1,3,5(10)-trien-17β-yl 3'-sulfamoylbenzoate,
17β-(n-Pentanoyloxy)estra-1,3,5(10)-trien-3-yl 3'-sulfamoylbenzoate,
17β-Benzoyloxyestra-1,3,5(10)-trien-3-yl 3'-sulfamoylbenzoate,
17β-Hydroxyestra-1,3,5(10)-trien-3-yl 4'-sulfamoylbenzoate,
17β-Hydroxyestra-1,3,5(10)-trien-3-yl 2',3'-dichloro-5'-sulfamoylbenzoate,
17β-Hydroxyestra-1,3,5(10)-trien-3-yl 2'-chloro-4'-fluoro-5'-sulfamoylbenzoate,
3-Methoxyestra-1,3,5(10)-trien-17β-yl 3'-sulfamoylbenzoate,
3-Hydroxyestra-1,3,5(10)-trien-17β-yl 2'-sulfamoylbenzoate,
3-Benzoyloxyestra-1,3,5(10)-trien-17β-yl 2'-sulfamoylbenzoate,
2-Methoxy-3-hydroxyestra-1,3,5(10)-trien-17β-yl 2',3'-dimethoxy-5'-sulfamoylbenzoate,
Estra-1,3,5(10)-triene-3,17β-diyl bis(3'-sulfamoylbenzoate),
2-Ethoxy-3-hydroxyestra-1,3,5(10)-trien-17β-yl 3'-sulfamoylbenzoate,
2-Ethoxy-3-hydroxyestra-1,3,5(10)-trien-17β-yl 2'-chloro-5'-sulfamoylbenzoate,
2-Ethoxy-3-hydroxyestra-1,3,5(10)-trien-17β-yl 3'-sulfamoyl-4'-chloro-benzoate,
2-Ethoxy-3-hydroxyestra-1,3,5(10)-trien-17β-yl 2',4'-dichloro-5'-sulfamoyl-benzoate,
2-Ethoxy-3-hydroxyestra-1,3,5(10)-trien-17β-yl 2'-chloro-4'-fluoro-5'-sulfamoylbenzoate,
2-Ethoxy-3-hydroxyestra-1,3,5(10)-trien-17β-yl 4'-sulfamoylbenzoate,
2-Ethoxy-3-hydroxyestra-1,3,5(10)-trien-17β-yl 4'-sulfamatobenzoate,
2-Ethoxy-3-hydroxyestra-1,3,5(10)-trien-17β-yl 2',3'-dimethoxy-5'-sulfamoylbenzoate,
3-tert.-Butyldimethylsilyloxyestra-1,3,5(10)-trien-17β-yl 2'-chloro-4'-sulfamoylbenzoate, or
3-Hydroxyestra-1,3,5(10)-trien-17β-yl 2'-chloro-4'-sulfamoylbenzoate,
or a pharmaceutically acceptable salt thereof.

17. A pharmaceutical composition comprising a compound according to claim 1 and a pharmaceutically acceptable carrier.

18. A pharmaceutical composition according to claim 17, further comprising a steroidally active compound which is not a compound of formula (I).

19. A pharmaceutical composition according to claim 18, wherein the additional steroidally active compound is a gestagen, an antigestagen or a mesoprogestin.

20. A pharmaceutical composition comprising a compound according to claim 12 and a pharmaceutically acceptable carrier.

21. A method for hormone replacement therapy in women, comprising administering to a subject in need thereof an effective amount of a pharmaceutical composition according to claim 17.

22. A method for birth control in women, comprising administering to a subject in need thereof an effective amount of a pharmaceutical composition according to claim 17.

23. A method for treating endometriosis, breast cancer, prostate cancer or hypogonadism, comprising administering to a subject in need thereof an effective amount of a pharmaceutical composition according to claim 17.

24. A method for hormone replacement therapy in women, comprising administering to a subject in need thereof an effective amount of a pharmaceutical composition according to claim 20.

25. A method for birth control in women, comprising administering to a subject in need thereof an effective amount of a pharmaceutical composition according to claim 20.

26. A method for treating endometriosis, breast cancer, prostate cancer or hypogonadism, comprising administering to a subject in need thereof an effective amount of a pharmaceutical composition according to claim 20.

* * * * *